US008034941B2

(12) United States Patent
Eckhardt et al.

(10) Patent No.: US 8,034,941 B2
(45) Date of Patent: *Oct. 11, 2011

(54) IMIDAZOPYRIDAZINONE AND IMIDAZOPYRIDONE DERIVATIVES, THE PREPARATION THEREOF AND THEIR USE AS PHARMACEUTICAL COMPOSITIONS

(75) Inventors: Matthias Eckhardt, Biberach (DE); Norbert Hauel, Schemmerhofen (DE); Elke Langkopf, Warthausen (DE); Frank Himmelsbach, Mittelbiberach (DE); Iris Kauffmann-Hefner, Attenweiler (DE); Mohammad Tadayyon, Watford (GB); Michael Mark, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 68 days.

This patent is subject to a terminal disclaimer.

(21) Appl. No.: 12/489,716

(22) Filed: Jun. 23, 2009

(65) Prior Publication Data

US 2009/0258856 A1 Oct. 15, 2009

Related U.S. Application Data

(62) Division of application No. 10/865,719, filed on Jun. 10, 2004, now Pat. No. 7,566,707.

(60) Provisional application No. 60/487,309, filed on Jul. 15, 2003.

(30) Foreign Application Priority Data

Jun. 18, 2003 (DE) .................................. 103 27 439

(51) Int. Cl.
*C07D 515/02* (2006.01)
(52) U.S. Cl. ......................................... 546/118
(58) Field of Classification Search .................... 546/118
See application file for complete search history.

(56) References Cited

U.S. PATENT DOCUMENTS

| | | | |
|---|---|---|---|
| 2,928,833 A | 3/1960 | Leake et al. | |
| 4,005,208 A | 1/1977 | Bender | |
| 4,599,338 A | 7/1986 | Regnier et al. | |
| 5,041,448 A | 8/1991 | Janssens | |
| 5,051,517 A | 9/1991 | Findeisen | |
| 5,223,499 A | 6/1993 | Greenlee | |
| 5,234,897 A | 8/1993 | Findeisen et al. | |
| 5,258,380 A | 11/1993 | Janssens et al. | |
| 5,266,555 A | 11/1993 | Findeisen et al. | |
| 5,389,642 A | 2/1995 | Dorsch et al. | |
| 5,470,579 A | 11/1995 | Bonte et al. | |
| 5,719,279 A | 2/1998 | Kufner-Muhl et al. | |
| 5,753,635 A | 5/1998 | Buckman | |
| 6,303,661 B1 | 10/2001 | Demuth | |
| 6,342,601 B1 | 1/2002 | Bantick | |
| 6,548,481 B1 | 4/2003 | Demuth | |
| 6,579,868 B1 | 6/2003 | Asano | |
| 6,784,195 B2 | 8/2004 | Hale et al. | |
| 6,821,978 B2 | 11/2004 | Chackalamannil | |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 * | 9/2006 | Hauel et al. .................. 514/218 |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 2002/0161001 A1 | 10/2002 | Kanstrup | |
| 2002/0169174 A1 | 11/2002 | Chackalamannil et al. | |
| 2002/0198205 A1 | 12/2002 | Himmelsbach | |
| 2003/0105077 A1 | 6/2003 | Kanstrup et al. | |
| 2003/0199528 A1 | 10/2003 | Kanstrup | |
| 2003/0232987 A1 | 12/2003 | Dahanukar | |
| 2003/0236272 A1 | 12/2003 | Carr | |
| 2004/0034014 A1 | 2/2004 | Kanstrup et al. | |
| 2004/0077645 A1 | 4/2004 | Himmelsbach et al. | |
| 2004/0082570 A1 | 4/2004 | Yoshikawa | |
| 2004/0087587 A1 | 5/2004 | Himmelsbach | |
| 2004/0097510 A1 | 5/2004 | Himmelsbach et al. | |

(Continued)

FOREIGN PATENT DOCUMENTS

CA          2136288 A1       5/1995

(Continued)

OTHER PUBLICATIONS

Wolff, Burger's medicinal Chemistry and Drug Discovery, vol. 1, Principles and Practice, John Wiley & sons, New York, 1997.*
U.S. Appl. No. 11/744,700, filed May 4, 2007, Sieger.
U.S. Appl. No. 11/744,701, filed May 4, 2007, Kohlrausch.
Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

(Continued)

Primary Examiner — Nizal Chandrakumar
(74) Attorney, Agent, or Firm — Michael P. Morris; Alan R. Stempel

(57) ABSTRACT

The present invention relates to substituted imidazo-pyridinones and imidazo-pyridazinones of general formula (I)

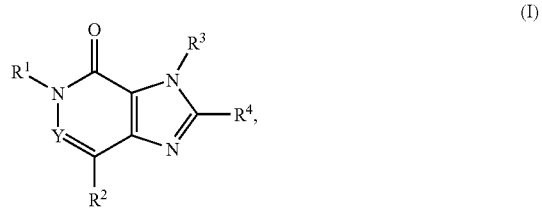

wherein Y and $R^1$ to $R^4$ are defined as in claim 1, the tautomers, enantiomers, diastereomers, the mixtures thereof and the salts thereof, which have valuable pharmacological properties, particularly an inhibiting effect on the activity of the enzyme dipeptidylpeptidase-IV (DPP-IV).

5 Claims, No Drawings

U.S. PATENT DOCUMENTS

| | | |
|---|---|---|
| 2004/0116328 A1 | 6/2004 | Yoshikawa et al. |
| 2004/0122228 A1 | 6/2004 | Maier |
| 2004/0138214 A1 | 7/2004 | Himmelsbach et al. |
| 2004/0138215 A1 | 7/2004 | Eckhardt |
| 2004/0166125 A1 | 8/2004 | Himmelsbach |
| 2005/0020574 A1 | 1/2005 | Hauel et al. |
| 2005/0026921 A1 | 2/2005 | Eckhardt |
| 2005/0130985 A1 | 6/2005 | Himmelsbach |
| 2005/0187227 A1 | 8/2005 | Himmelsbach et al. |
| 2005/0203095 A1 | 9/2005 | Eckhardt |
| 2005/0234108 A1 | 10/2005 | Himmelsbach et al. |
| 2005/0261352 A1 | 11/2005 | Eckhardt |
| 2006/0004074 A1 | 1/2006 | Eckhardt |
| 2006/0058323 A1 | 3/2006 | Eckhardt |
| 2006/0063787 A1 | 3/2006 | Yoshikawa |
| 2006/0079541 A1 | 4/2006 | Langkopf |
| 2006/0094722 A1 | 5/2006 | Yasuda |
| 2006/0100199 A1 | 5/2006 | Yoshikawa et al. |
| 2006/0142310 A1 | 6/2006 | Pfrengle et al. |
| 2006/0173056 A1 | 8/2006 | Kitajima et al. |
| 2006/0205711 A1 | 9/2006 | Himmelsbach et al. |
| 2006/0247226 A1 | 11/2006 | Himmelsbach et al. |
| 2007/0027168 A1 | 2/2007 | Pfrengle et al. |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0185091 A1 | 8/2007 | Himmelsbach et al. |
| 2007/0219178 A1 | 9/2007 | Muramoto |
| 2007/0281940 A1 | 12/2007 | Dugi et al. |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | 02/02560 A2 | 1/2002 |
| WO | 02/14271 A1 | 2/2002 |
| WO | 02/24698 A1 | 3/2002 |
| WO | 02/068420 A1 | 9/2002 |
| WO | 03/004496 A1 | 1/2003 |
| WO | 03/024965 A1 | 3/2003 |
| WO | 03/057200 A2 | 7/2003 |
| WO | 03/104229 A1 | 12/2003 |
| WO | 2004/018467 A2 | 3/2004 |
| WO | 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | 2004/050658 A1 | 6/2004 |
| WO | 2004/096806 A1 | 11/2004 |
| WO | 2004/108730 A1 | 12/2004 |
| WO | 2004/111051 A1 | 12/2004 |
| WO | 2005/058901 A1 | 6/2005 |
| WO | 2005/082906 A1 | 9/2005 |
| WO | 2005/085246 A1 | 9/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |
| WO | 2008/017670 A1 | 2/2008 |

OTHER PUBLICATIONS

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Busso et al., "Circulating CD26 is Negatively Associated with Inflammation in Human and Experimental Arthritis," Am. J. Path., vol. 166, No. 2, Feb. 2005, pp. 433-442.

Caira, M.R., "Crystalline polymorphism of organic compounds" Topics in Current Chemistry, Springer, Berlin, vol. 198, 1998, p. 163-208.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Deacon, C.F. et al; "Dipeptidyl peptidase IV inhabitation as an approach to the treatment and prevention of type 2 diabetes: a historical perspective;" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Januvia; Patient Information; Oct. 2007.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Patani George A. et al.: "Bioisoterism : A Rational Approach in Drug Design", Chemical Reviews, 1996, vol. 96, No. 8, pp. 3147-3176.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Yoshikawa, Seiji et al.: Chemical Abstract of Japanese Patent No. WO 2003/104229 Preparation of purinone derivatives as dipeptidylpeptidase IV (DPP-IV) inhibitors.

Zejc, Alfred et al; "Badania Nad Piperazynowymi Pochodnymi Dwumetyloksantyn" Acta Polon Pharm, XXXV, Nr. 4, 1976, pp. 417-421.

Zhong, Qing et al; "Glucose-dependent insulinotropic peptide stimulates proliferation and TGF-β release from MG-63 cells," Peptides 24 (2003) 611-616.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

* cited by examiner

IMIDAZOPYRIDAZINONE AND IMIDAZOPYRIDONE DERIVATIVES, THE PREPARATION THEREOF AND THEIR USE AS PHARMACEUTICAL COMPOSITIONS

RELATED APPLICATIONS

This application is a divisional of U.S. application Ser. No. 10/865,719, filed Jun. 10, 2004, now allowed, which claims benefit of U.S. Ser. No. PV 60/487,309, filed Jul. 15, 2003, and claims priority to German Application No. DE 10327439.1 filed Jun. 18, 2003, each of which is hereby incorporated by reference in its entirety.

The present invention relates to new substituted imidazopyridazinones and imidazopyridones of general formula

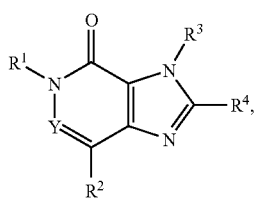

(I)

the tautomers, the enantiomers, the diastereomers, the mixtures thereof, the prodrugs thereof and the salts thereof, particularly the physiologically acceptable salts thereof with inorganic or organic acids or bases which have valuable pharmacological properties, particularly an inhibiting effect on the activity of the enzyme dipeptidylpeptidase-IV (DPP-IV), the preparation thereof, the use thereof for the prevention or treatment of diseases or conditions associated with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof as well as processes for the preparation thereof.

The present invention thus relates to the above compounds of general formula I which have valuable pharmacological properties, the pharmaceutical compositions containing the pharmacologically effective compounds, the use thereof and processes for the preparation thereof.

In the above general formula I
$R^1$ denotes a $C_{1-3}$-alkyl group substituted by a group $R_a$, where
  $R_a$ denotes a 3,4-dihydro-quinolinyl, 3,4-dihydro-isoquinolinyl, 1,4-dihydro-quinazolinyl, 3,4-dihydroquinazolinyl, 1H-benzo[d][1,2]oxazinyl, 4H-benzo[e][1,3]-oxazinyl, 4H-benzo[d][1,3]oxazinyl or 2H-benzo[1,4]oxazinyl group, wherein in each case
    in the benzo moiety one to three methyne groups may each be replaced by a nitrogen atom and in the heterocyclyl moiety a methylene group may be replaced by a carbonyl group,
  a 4H-benzo[e][1,3]thiazinyl, 4H-benzo[d][1,3]thiazinyl or 2H-benzo[1,4]thiazinyl group wherein in each case
    in the benzo moiety one to three methyne groups may each be replaced by a nitrogen atom and in the heterocyclyl moiety a methylene group may be replaced by a carbonyl group and the sulphur atom may be replaced by a sulphinyl or sulphonyl group,
  a 2-oxo-2H-benzo[e][1,3]oxazinyl or 2,2-dioxo-1H-benzo[c][1,2]thiazinyl group wherein in each case in the benzo moiety
    one to three methyne groups may each be replaced by a nitrogen atom,
  a 2,3-dihydro-1H-benzo[e][1,4]diazepinyl, 4,5-dihydro-3H-benzo[b][1,4]diazepinyl or 5-oxo-4,5-dihydro-3H-benzo[e][1,4]diazepinyl group wherein in each case
    in the benzo moiety one to three methyne groups may each be replaced by a nitrogen atom and in the heterocyclyl moiety a methylene group may be replaced by a carbonyl group,
  a 2,3-dihydro-benzo[f][1,4]oxazepinyl or 2,3-dihydrobenzo[b][1,4]oxazepinyl group wherein in each case
    in the benzo moiety one to three methyne groups may each be replaced by a nitrogen atom and in the heterocyclyl moiety a methylene group may be replaced by a carbonyl group,
  a 2,3-dihydro-benzo[b][1,4]thiazepinyl or 2,3-dihydrobenzo[f][1,4]thiazepinyl group wherein in each case
    in the benzo moiety one to three methyne groups may each be replaced by a nitrogen atom and in the heterocyclyl moiety a methylene group may be replaced by a carbonyl group and the sulphur atom may be replaced by a sulphinyl or sulphonyl group,
  a 5-oxo-4,5-dihydro-benzo[f][1,3,4]oxadiazepinyl group wherein
    in the benzo moiety one to three methyne groups may each be replaced by a nitrogen atom,
  a 11H-dibenzo[b,e]azepinyl or 5H-dibenzo[a,d]cycloheptenyl group wherein in each case
    in the benzo moiety one to three methyne groups may each be replaced by a nitrogen atom and the methylene group in the heterocyclyl moiety may be replaced by an oxygen or sulphur atom, a carbonyl, sulphinyl or sulphonyl group or by an imino group substituted by $R_x$, where
      $R_x$ denotes a hydrogen atom or a $C_{1-4}$-alkyl, $C_{2-4}$-alkenyl, $C_{2-4}$-alkynyl, $C_{3-6}$-cycloalkyl, $C_{3-6}$-cycloalkyl-$C_{1-3}$-alkyl, aryl, aryl-$C_{1-3}$-alkyl, hydroxy-$C_{2-4}$-alkyl, $C_{1-3}$-alkyloxy-$C_{2-4}$-alkyl, $C_{3-6}$-cycloalkyloxy-$C_{2-4}$-alkyl, amino-$C_{2-4}$-alkyl, $C_{1-3}$-alkylamino-$C_{2-4}$-alkyl, di-($C_{1-3}$-alkyl)-amino-$C_{2-4}$-alkyl, $C_{1-3}$-alkyl-carbonyl, $C_{1-3}$-alkyloxy-carbonyl, $C_{1-3}$-alkyloxy-carbonyl-$C_{1-3}$-alkyl, aryl-carbonyl, $C_{1-3}$-alkyl-sulphonyl or aryl-sulphonyl group,
  a phenanthridinyl group wherein
    in the benzo moiety one to three methyne groups may each be replaced by a nitrogen atom, and
  a 1,2,3,4-tetrahydro-phenanthridinyl, 1,2,3,4,4a,10b-hexahydro-phenanthridinyl, 2,3-dihydro-1H-4-aza-cyclopenta[a]naphthyl or a 8,9,10,11-tetrahydro-7H-6-aza-cyclohepta[a]naphthyl group wherein in each case
    in the benzo moiety one to three methyne groups may each be replaced by a nitrogen atom and one or two methylene groups may each be replaced by an oxygen atom or a carbonyl group, while, if two methylene groups are each replaced by an oxygen atom, the oxygen atoms must be separated from one another by at least two methylene units,
  a phenanthrenyl group wherein
    in each case one to three of the methyne groups in position 1 to 4 and 5 to 8 may each be replaced by a nitrogen atom,
  a 1,2,3,4-tetrahydro-phenanthrenyl or a 1,2,3,4,5,6,7,8-octahydro-phenanthrenyl group wherein
    in each case one or two of the methylene groups in position 1 to 4 and 5 to 8 may each be replaced by an oxygen atom or a carbonyl group, while, if two methylene groups are each replaced by an oxygen atom, the oxygen atoms must be separated from one another by at least two methylene units, a 5H-benzo[e]pyrrolo[1,2-a][1,4]diazepinyl, thieno[3,2-b][1,4]benzoxazepinyl, 5H-dibenzo[d,f][1,3]diazepinyl or a 5-oxa-7-aza-dibenzo[a,c]cycloheptenyl group wherein in each case
  in the benzo moiety one to three methyne groups may each be replaced by a nitrogen atom, a naphtho[1,2-d]oxazolyl, naphtho[2,1-d]oxazolyl, naphtho[1,2-d]thiazolyl, naphtho[2,1-d]thiazolyl, naphtho[1,2-d]imidazolyl, naphtho[1,2-b]furanyl or naphtho[2,1-b]furanyl group wherein in each case
  in the naphthyl moiety one to three methyne groups may each be replaced by a nitrogen atom, or a furo[3,2-c]isoquinolinyl, pyrazolo[1,5-c]quinazolinyl or 1H-perimidinyl group, while the methylene and methyne groups of the above mentioned radicals $R_a$ may be substituted by the groups $R^{10}$ to $R^{13}$ and additionally by a $C_{1-3}$-alkyl group and the imino groups of the above mentioned radicals $R_a$ may be substituted by the groups $R_x$ as hereinbefore defined and $R^{10}$ denotes a hydrogen atom,
a fluorine, chlorine, bromine or iodine atom,
a $C_{1-4}$-alkyl, hydroxy, or $C_{1-4}$-alkyloxy group,
a nitro, amino, $C_{1-3}$-alkylamino, di-($C_{1-3}$-alkyl)amino, cyano-$C_{1-3}$-alkylamino, N-(cyano-$C_{1-3}$-alkyl)-N—($C_{1-3}$-alkyl)-amino, $C_{1-3}$-alkyloxy-carbonyl-$C_{1-3}$-alkylamino, pyrrolidin-1-yl, piperidin-1-yl, morpholin-4-yl, piperazin-1-yl, or 4-($C_{1-3}$-alkyl)-piperazin-1-yl group,
a $C_{1-3}$-alkyl-carbonylamino, arylcarbonylamino, aryl-$C_{1-3}$-alkyl-carbonylamino, $C_{1-3}$-alkyloxy-carbonylamino, aminocarbonylamino, $C_{1-3}$-alkylaminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino or 4-($C_{1-3}$-alkyl)-piperazin-1-yl-carbonylamino, $C_{1-3}$-alkyl-sulphonylamino, bis-($C_{1-3}$-alkylsulphonyl)-amino, aminosulphonylamino, $C_{1-3}$-alkylamino-sulphonylamino, di-($C_{1-3}$-alkyl)amino-sulphonylamino, pyrrolidin-1-yl-sulphonylamino, piperidin-1-yl-sulphonylamino, morpholin-4-yl-sulphonylamino, piperazin-1-yl-sulphonylamino or 4-($C_{1-3}$-alkyl)-piperazin-1-yl-sulphonylamino, ($C_{1-3}$-alkylamino)thiocarbonylamino, ($C_{1-3}$-alkyloxy-carbonylamino)carbonylamino, arylsulphonylamino or aryl-$C_{1-3}$-alkyl-sulphonylamino group,
an N—($C_{1-3}$-alkyl)-$C_{1-3}$-alkyl-carbonylamino, N—($C_{1-3}$-alkyl)-arylcarbonylamino, N—($C_{1-3}$-alkyl)-aryl-$C_{1-3}$-alkyl-carbonylamino, N—($C_{1-3}$-alkyl)-$C_{1-3}$-alkyloxy-carbonylamino, N-(aminocarbonyl)-$C_{1-3}$-alkylamino, N—($C_{1-3}$-alkyl-aminocarbonyl)-$C_{1-3}$-alkylamino, N—[di-($C_{1-3}$-alkyl)aminocarbonyl]-$C_{1-3}$-alkylamino, N—($C_{1-3}$-alkyl)-$C_{1-3}$-alkyl-sulphonylamino, N—($C_{1-3}$-alkyl)-arylsulphonylamino, or N—($C_{1-3}$-alkyl)-aryl-$C_{1-3}$-alkyl-sulphonylamino group,
a 2-oxo-imidazolidin-1-yl, 2,4-dioxo-imidazolidin-1-yl, 2,5-dioxo-imidazolidin-1-yl or 2-oxo-hexahydropyrimidin-1-yl group wherein the nitrogen atom in the 3 position may be substituted in each case by a methyl or ethyl group,
a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-($C_{1-3}$-alkyl)-piperazin-1-yl-carbonyl group,
a $C_{1-3}$-alkyl-carbonyl or an arylcarbonyl group,
a carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl or 4-($C_{1-3}$-alkyl)-piperazin-1-yl-carbonyl-$C_{1-3}$-alkyl group,
a carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyloxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy or 4-($C_{1-3}$-alkyl)-piperazin-1-yl-carbonyl-$C_{1-3}$-alkyloxy group,
a hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, piperidin-1-yl-$C_{1-3}$-alkyl, morpholin-4-yl-$C_{1-3}$-alkyl, piperazin-1-yl-$C_{1-3}$-alkyl or 4-($C_{1-3}$-alkyl)-piperazin-1-yl-$C_{1-3}$-alkyl group,
a hydroxy-$C_{1-3}$-alkyloxy, $C_{1-3}$-alkyloxy-$C_{1-3}$-alkyloxy, $C_{1-3}$-alkylsulphanyl-$C_{1-3}$-alkyloxy, $C_{1-3}$-alkylsulphinyl-$C_{1-3}$-alkyloxy, $C_{1-3}$-alkylsulphonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, morpholin-4-yl-$C_{1-3}$-alkyloxy, piperazin-1-yl-$C_{1-3}$-alkyloxy or 4-($C_{1-3}$-alkyl)-piperazin-1-yl-$C_{1-3}$-alkyloxy group,
a mercapto, $C_{1-3}$-alkylsulphanyl, $C_{1-3}$-alkysulphinyl, $C_{1-3}$-alkylsulphonyl, $C_{1-3}$-alkylsulphonyloxy, arylsulphonyloxy, trifluoromethylsulphanyl, trifluoromethylsulphinyl or trifluoromethylsulphonyl group,
a sulpho, aminosulphonyl, $C_{1-3}$-alkyl-aminosulphonyl, di-($C_{1-3}$-alkyl)-aminosulphonyl, pyrrolidin-1-yl-sulphonyl, piperidin-1-yl-sulphonyl, morpholin-4-yl-sulphonyl, piperazin-1-yl-sulphonyl or 4-($C_{1-3}$-alkyl)-piperazin-1-yl-sulphonyl group,
a methyl or methoxy group substituted by 1 to 3 fluorine atoms,
an ethyl or ethoxy group substituted by 1 to 5 fluorine atoms,
a $C_{2-4}$-alkenyl or $C_{2-4}$-alkynyl group,
a $C_{3-4}$-alkenyloxy or $C_{3-4}$-alkynyloxy group,
a $C_{3-6}$-cycloalkyl or $C_{3-6}$-Cycloalkyloxy group,
a $C_{3-6}$-cycloalkyl-$C_{1-3}$-alkyl or $C_{3-6}$-cycloalkyl-$C_{1-3}$-alkyloxy group or
an aryl, aryloxy, aryl-$C_{1-3}$-alkyl or aryl-$C_{1-3}$-alkyloxy group,
$R^{11}$ and $R^{12}$, which may be identical or different, in each case represent a hydrogen atom, a fluorine, chlorine, bromine or iodine atom, a $C_{1-3}$-alkyl, trifluoromethyl, hydroxy, $C_{1-3}$-alkyloxy or cyano group, or
$R^{11}$ together with $R^{12}$, if these are bound to adjacent carbon atoms, also denotes a methylenedioxy, difluoromethylenedioxy, ethylenedioxy or a straight-chain $C_{3-5}$-alkylene group and
$R^{13}$ denotes a hydrogen atom, a fluorine, chlorine or bromine atom, a trifluoromethyl, $C_{1-3}$-alkyl or $C_{1-3}$-alkyloxy group, $R^2$ denotes a hydrogen, fluorine or chlorine atom,
a $C_{1-6}$-alkyl group,
a $C_{2-4}$-alkenyl group,
a $C_{3-4}$-alkynyl group,
a $C_{3-6}$-cycloalkyl group,
a $C_{3-6}$-cycloalkyl-$C_{1-3}$-alkyl group,
a tetrahydrofuran-3-yl, tetrahydropyran-3-yl, tetrahydropyran-4-yl, tetrahydrofuranylmethyl or tetrahydropyranylmethyl group,
an aryl group,
an aryl-$C_{1-4}$-alkyl group,
an aryl-$C_{2-3}$-alkenyl group,
an arylcarbonyl group,
an arylcarbonyl-$C_{1-2}$-alkyl group,
a heteroaryl group,
a heteroaryl-$C_{1-3}$-alkyl group,
a furanylcarbonyl, thienylcarbonyl, thiazolylcarbonyl or pyridylcarbonyl group,
a furanylcarbonylmethyl, thienylcarbonylmethyl, thiazolylcarbonylmethyl or pyridylcarbonylmethyl group,
a $C_{1-4}$-alkyl-carbonyl group,
a $C_{1-4}$-alkyl-carbonyl-$C_{1-2}$-alkyl group,
a $C_{3-6}$-cycloalkyl-carbonyl group,
a $C_{3-6}$-cycloalkyl-carbonyl-$C_{1-2}$-alkyl group,
an aryl-A or aryl-A-$C_{1-3}$-alkyl group, where A denotes an oxygen or sulphur atom, an imino, $C_{1-3}$-alkylimino, sulphinyl or sulphonyl group,
a group $R_b$, where
  $R_b$ denotes a cyano, carboxy, $C_{1-3}$-alkyloxy-carbonyl, aminocarbonyl, $C_{1-3}$-alkylamino-carbonyl, di-($C_{1-3}$-alkyl)-amino-carbonyl, pyrrolidin-1-ylcarbonyl, piperidin-1-ylcarbonyl, morpholin-4-ylcarbonyl, piperazin-1-ylcarbonyl, 4-methylpiperazin-1-ylcarbonyl, 4-ethylpiperazin-1-ylcarbonyl, hydroxy, mercapto, $C_{1-3}$-alkyloxy, $C_{1-3}$-alkylsulphenyl, $C_{1-3}$-alkylsulphinyl, $C_{1-3}$-alkylsulphonyl, amino, $C_{1-3}$-alkylamino, di-($C_{1-3}$-alkyl)-amino, pyrrolidin-1-yl, piperidin-1-yl, morpholin-4-yl, piperazin-1-yl, 4-methyl-piperazin-1-yl or 4-ethyl-piperazin-1-yl group,
or a $C_{1-4}$-alkyl group substituted by a group $R_b$, where $R_b$ is as hereinbefore defined,
Y denotes a nitrogen atom or a group of formula C—$R^5$,
  while $R^5$ is defined like $R^2$ and in each case one of the two groups $R^2$ and $R^5$ must be a hydrogen atom or a $C_{1-3}$-alkyl group,
$R^3$ denotes a $C_{3-8}$-alkyl group,
a $C_{1-3}$-alkyl group substituted by a group $R_c$, where
  $R_c$ denotes a $C_{3-7}$-cycloalkyl group optionally substituted by one or two $C_{1-3}$-alkyl groups,
  a $C_{5-7}$-cycloalkenyl group optionally substituted by one or two $C_{1-3}$-alkyl groups,
  an aryl group or
  a furanyl, thienyl, oxazolyl, isoxazolyl, thiazolyl, isothiazolyl, pyridyl, pyridazinyl, pyrimidyl or pyrazinyl group, while the above mentioned heterocyclic groups may each be substituted by one or two $C_{1-3}$-alkyl groups or by a fluorine, chlorine, bromine or iodine atom or by a trifluoromethyl, cyano or $C_{1-3}$-alkyloxy group,
a $C_{3-8}$-alkenyl group,
a $C_{3-6}$-alkenyl group substituted by a fluorine, chlorine or bromine atom or by a trifluoromethyl group,
a $C_{3-8}$-alkynyl group,
an aryl group or
an aryl-$C_{2-4}$-alkenyl group,
and
$R^4$ denotes an azetidin-1-yl or pyrrolidin-1-yl group which is substituted in the 3 position by an amino, $C_{1-3}$-alkylamino or a di-($C_{1-3}$-alkyl)amino group and may additionally be substituted by one or two $C_{1-3}$-alkyl groups,
a piperidin-1-yl or hexahydroazepin-1-yl group which is substituted in the 3 position or in the 4 position by an amino, $C_{1-3}$-alkylamino or a di-($C_{1-3}$-alkyl)amino group and may additionally be substituted by one or two $C_{1-3}$-alkyl groups,
a 3-amino-piperidin-1-yl group wherein the piperidin-1-yl moiety is additionally substituted by an aminocarbonyl, $C_{1-2}$-alkyl-aminocarbonyl, di-($C_{1-2}$-alkyl)aminocarbonyl, pyrrolidin-1-yl-carbonyl, (2-cyano-pyrrolidin-1-yl-)carbonyl, thiazolidin-3-yl-carbonyl, (4-cyano-thiazolidin-3-yl)carbonyl, piperidin-1-ylcarbonyl or morpholin-4-ylcarbonyl group,
a 3-amino-piperidin-1-yl group wherein the piperidin-1-yl moiety in the 4 position or in the 5 position is additionally substituted by a hydroxy or methoxy group,
a 3-amino-piperidin-1-yl group wherein the methylene group in the 2 position or in the 6 position is replaced by a carbonyl group,
a piperidin-1-yl or hexahydroazepin-1-yl group substituted in the 3 position by an amino, $C_{1-3}$-alkylamino or di-($C_{1-3}$-alkyl)-amino-group, wherein in each case two hydrogen atoms on the carbon skeleton of the piperidin-1-yl or hexahydroazepin-1-yl-group are replaced by a straight-chain alkylene bridge, this bridge containing 2 to 5 carbon atoms if the two hydrogen atoms are located on the same carbon atom, or 1 to 4 carbon atoms, if the hydrogen atoms are located on adjacent carbon atoms, or 1 to 4 carbon atoms, if the hydrogen atoms are located on carbon atoms which are separated by one atom, or 1 to 3 carbon atoms if the two hydrogen atoms are located on carbon atoms separated by two atoms,
an azetidin-1-yl, pyrrolidin-1-yl, piperidin-1-yl or hexahydroazepin-1-yl group which is substituted by an amino-$C_{1-3}$-alkyl, $C_{1-3}$-alkylamino-$C_{1-3}$-alkyl or a di-($C_{1-3}$-alkyl)-amino-$C_{1-3}$-alkyl group,
a piperazin-1-yl or [1,4]diazepan-1-yl group optionally substituted at the carbon skeleton by one or two $C_{1-3}$-alkyl groups,
a 3-imino-piperazin-1-yl, 3-imino-[1,4]diazepan-1-yl or 5-imino-[1,4]diazepan-1-yl group optionally substituted at the carbon skeleton by one or two $C_{1-3}$-alkyl groups,
a [1,4]diazepan-1-yl group optionally substituted by one or two $C_{1-3}$-alkyl groups, which is substituted in the 6 position by an amino group,
a $C_{3-7}$-cycloalkyl group which is substituted by an amino, $C_{1-3}$-alkylamino or di-($C_{1-3}$-alkyl)-amino group,
a $C_{3-7}$-cycloalkyl group which is substituted by an amino-$C_{1-3}$-alkyl, $C_{1-3}$-alkylamino-$C_{1-3}$-alkyl or a di-($C_{1-3}$-alkyl) amino-$C_{1-3}$-alkyl group,
a $C_{3-7}$-cycloalkyl-$C_{1-2}$-alkyl group wherein the cycloalkyl moiety is substituted by an amino, $C_{1-3}$-alkylamino or di-($C_{1-3}$-alkyl)-amino group,
a $C_{3-7}$-cycloalkyl-$C_{1-2}$-alkyl group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group,
a $C_{3-7}$-cycloalkylamino group wherein the cycloalkyl moiety is substituted by an amino, $C_{1-3}$-alkylamino or di-($C_{1-3}$-alkyl)-amino group, while the two nitrogen atoms at the cycloalkyl moiety are separated from one another by at least two carbon atoms,
an N—($C_{3-7}$-cycloalkyl)-N—($C_{1-3}$-alkyl)-amino group wherein the cycloalkyl moiety is substituted by an amino, $C_{1-3}$-alkylamino or di-($C_{1-3}$-alkyl)-amino group, while the two nitrogen atoms at the cycloalkyl moiety are separated from one another by at least two carbon atoms, a $C_{3-7}$-cycloalkylamino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N—($C_{3-7}$-cycloalkyl)-N—($C_{1-3}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $C_{3-7}$-cycloalkyl-$C_{1-2}$-alkyl-amino group wherein the cycloalkyl moiety is substituted by an amino, $C_{1-3}$-alkylamino or di-($C_{1-3}$-alkyl)-amino group, an N—($C_{3-7}$-cycloalkyl-$C_{1-2}$-alkyl)-N—($C_{1-2}$-alkyl)-amino group wherein the cycloalkyl moiety is substituted by an amino, $C_{1-3}$-alkylamino or di-($C_{1-3}$-alkyl)-amino group, a $C_{3-7}$-cycloalkyl-$C_{1-2}$-alkyl-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, an N—($C_{3-7}$-cycloalkyl-$C_{1-2}$-alkyl)-N—($C_{1-2}$-alkyl)-amino group wherein the cycloalkyl moiety is substituted by an amino-$C_{1-3}$-alkyl, $C_{1-3}$-alkylamino-$C_{1-3}$-alkyl or a di-($C_{1-3}$-alkyl)amino-$C_{1-3}$-alkyl group, a $R^{19}$—$C_{2-4}$-alkylamino group wherein $R^{19}$ is separated from the nitrogen atom of the $C_{2-4}$-alkylamino moiety by at least two carbon atoms and $R^{19}$ denotes an amino, $C_{1-3}$-alkylamino or di-($C_{1-3}$-alkyl)-amino group, an $R^{19}$—$C_{2-4}$-alkylamino group wherein the nitrogen atom of the $C_{2-4}$-alkylamino moiety is substituted by a $C_{1-3}$-alkyl group and $R^{19}$ is separated from the nitrogen atom of the $C_{2-4}$-alkylamino moiety by at least two carbon atoms, while $R^{19}$ is as hereinbefore defined, an amino group substituted by the group $R^{20}$ wherein $R^{20}$ denotes an azetidin-3-yl, azetidin-2-ylmethyl, azetidin-3-ylmethyl, pyrrolidin-3-yl, pyrrolidin-2-ylmethyl, pyrrolidin-3-ylmethyl, piperidin-3-yl, piperidin-4-yl, piperidin-2-ylmethyl, piperidin-3-ylmethyl or piperidin-4-ylmethyl group, while the groups mentioned for $R^{20}$ may each be substituted by one or two $C_{1-3}$-alkyl groups, an amino group substituted by the group $R^{20}$ and a $C_{1-3}$-alkyl group wherein $R^{20}$ is as hereinbefore defined, while the groups mentioned for $R^{20}$ may each be substituted by one or two $C_{1-3}$-alkyl groups, an $R^{19}$—$C_{3-4}$-alkyl group wherein the $C_{3-4}$-alkyl moiety is straight-chained and may additionally be substituted by one or two $C_{1-3}$-alkyl groups, while $R^{19}$ is as hereinbefore defined, a 3-amino-2-oxo-piperidin-5-yl or 3-amino-2-oxo-1-methyl-piperidin-5-yl group, a pyrrolidin-3-yl, piperidin-3-yl, piperidin-4-yl, hexahydroazepin-3-yl or hexahydroazepin-4-yl group which is substituted in the 1 position by an amino, $C_{1-3}$-alkylamino or di-($C_{1-3}$-alkyl)amino group, or an azetidin-2-yl-$C_{1-2}$-alkyl, azetidin-3-yl-$C_{1-2}$-alkyl, pyrrolidin-2-yl-$C_{1-2}$-alkyl, pyrrolidin-3-yl, pyrrolidin-3-yl-$C_{1-2}$-alkyl, piperidin-2-yl-$C_{1-2}$-alkyl, piperidin-3-yl, piperidin-3-yl-$C_{1-2}$-alkyl, piperidin-4-yl or piperidin-4-yl-$C_{1-2}$-alkyl group, while the above mentioned groups may each be substituted by one or two $C_{1-3}$-alkyl groups, while by the aryl groups mentioned in the definition of the above groups are meant phenyl or naphthyl groups which may be mono- or disubstituted by $R_h$, while the substituents may be identical or different and $R_h$ denotes a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-3}$-alkyl, cyclopropyl, ethenyl, ethynyl, hydroxy, $C_{1-3}$-alkyloxy, difluoromethoxy or trifluoromethoxy group, by the heteroaryl groups mentioned in the definition of the above groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, and the above mentioned heteroaryl groups may be mono- or disubstituted by $R_h$, while the substituents may be identical or different and $R_h$ is as hereinbefore defined, while, unless otherwise stated, the above mentioned alkyl, alkenyl and alkynyl groups may be straight-chain or branched, and the hydrogen atoms of the methyl or ethyl groups contained in the definitions may be wholly or partly replaced by fluorine atoms, the tautomers, enantiomers, diastereomers, the mixtures thereof, the prodrugs thereof and the salts thereof.

Compounds of the above general formula I which contain one or more groups that can be cleaved in vivo are so-called prodrugs.

The carboxy groups mentioned in the definition of the above mentioned groups may be replaced by a group which can be converted into a carboxy group in vivo or by a group which is negatively charged under physiological conditions, and furthermore the amino and imino groups mentioned in the definition of the above mentioned groups may be substituted by a group which can be cleaved in vivo. Such groups are described for example in WO 98/46576 and by N. M. Nielsen et al. in International Journal of Pharmaceutics 39, 75-85 (1987).

By a group which can be converted in vivo into a carboxy group is meant, for example, a hydroxymethyl group, a carboxy group esterified with an alcohol wherein the alcohol moiety is preferably a $C_{1-6}$-alkanol, a phenyl-$C_{1-3}$-alkanol, a $C_{3-9}$-cycloalkanol, while a $C_{5-8}$-cycloalkanol may additionally be substituted by one or two $C_{1-3}$-alkyl groups, a $C_{5-8}$-cycloalkanol wherein a methylene group in the 3 or 4 position is replaced by an oxygen atom or by an imino group optionally substituted by a $C_{1-3}$-alkyl, phenyl-$C_{1-3}$-alkyl, phenyl-$C_{1-3}$-alkyloxycarbonyl or $C_{2-6}$-alkanoyl group and the cycloalkanol moiety may additionally be substituted by one or two $C_{1-3}$-alkyl groups, a $C_{4-7}$-cycloalkenol, a $C_{3-5}$-alkenol, a phenyl-$C_{3-5}$-alkenol, a $C_{3-5}$-alkynol or phenyl-$C_{3-5}$-alkynol with the proviso that no bonds to the oxygen atom start from a carbon atom which carries a double or triple bond, a $C_{3-8}$-cycloalkyl-$C_{1-3}$-alkanol, a bicycloalkanol with a total of 8 to 10 carbon atoms which may additionally be substituted in the bicycloalkyl moiety by one or two $C_{1-3}$-alkyl groups, a 1,3-dihydro-3-oxo-1-isobenzofuranol or an alcohol of formula $$R_p—CO—O—(R_qCR_r)—OH,$$

wherein $R_p$ denotes a $C_{1-8}$-alkyl, $C_{5-7}$-cycloalkyl, $C_{1-8}$-alkyloxy, $C_{5-7}$-cycloalkyloxy, phenyl or phenyl-$C_{1-3}$-alkyl group, $R_q$ denotes a hydrogen atom, a $C_{1-3}$-alkyl, $C_{5-7}$-cycloalkyl or phenyl group and $R_r$ denotes a hydrogen atom or a $C_{1-3}$-alkyl group, by a group which is negatively charged under physiological conditions is meant, for example, a tetrazol-5-yl, phenylcarbonylaminocarbonyl, trifluoromethylcarbonylaminocarbonyl, $C_{1-6}$-alkylsulphonylamino, phenylsulphonylamino, benzylsulphonylamino, trifluoromethylsulphonylamino, $C_{1-6}$-alkylsulphonylaminocarbonyl, phenylsulphonylaminocarbonyl, benzylsulphonylaminocarbonyl or perfluoro-$C_{1-6}$-alkylsulphonylaminocarbonyl group and by a group which can be cleaved in vivo from an imino or amino group is meant, for example, a hydroxy group, an acyl group such as a phenylcarbonyl group optionally mono- or disubstituted by fluorine, chlorine, bromine or iodine atoms, by $C_{1-3}$-alkyl or $C_{1-3}$-alkyloxy groups, while the substituents may be identical or different, a pyridinoyl group or a $C_{1-16}$-alkanoyl group such as the formyl, acetyl, propionyl, butanoyl, pentanoyl or hexanoyl group, a 3,3,3-trichloropropionyl or allyloxycarbonyl group, a $C_{1-16}$-alkyloxycarbonyl or $C_{1-6}$-alkylcarbonyloxy group, wherein hydrogen atoms may be wholly or partially replaced by fluorine or chlorine atoms such as the methoxycarbonyl, ethoxycarbonyl, propoxycarbonyl, isopropoxycarbonyl, butoxycarbonyl, tert.butoxycarbonyl, pentoxycarbonyl, hexoxycarbonyl, octyloxycarbonyl, nonyloxycarbonyl, decyloxycarbonyl, undecyloxycarbonyl, dodecyloxycarbonyl, hexadecyloxycarbonyl, methylcarbonyloxy, ethylcarbonyloxy, 2,2,2-trichloroethylcarbonyloxy, propylcarbonyloxy, isopropylcarbonyloxy, butylcarbonyloxy, tert.butylcarbonyloxy, pentylcarbonyloxy, hexylcarbonyloxy, octylcarbonyloxy, nonylcarbonyloxy, decylcarbonyloxy, undecylcarbonyloxy, dodecylcarbonyloxy or hexadecylcarbonyloxy group, a phenyl-$C_{1-6}$-alkyloxycarbonyl group such as the benzyloxycarbonyl, phenylethoxycarbonyl or phenylpropoxycarbonyl group, a 3-amino-propionyl group wherein the amino group may be mono- or disubstituted by $C_{1-6}$-alkyl or $C_{3-7}$-cycloalkyl groups and the substituents may be identical or different, a $C_{1-3}$-alkylsulphonyl-$C_{2-4}$-alkyloxycarbonyl, $C_{1-3}$-alkyloxy-$C_{2-4}$-alkyloxy-$C_{2-4}$-alkyloxycarbonyl, $R_p$—CO—O—($R_qCR_r$)—O—CO, $C_{1-6}$-alkyl-CO—NH—($R_sCR_t$)—O—CO or $C_{1-6}$-alkyl-CO—O—($R_sCR_t$)—($R_sCR_t$)—O—CO group, wherein $R_p$ to $R_r$ are as hereinbefore defined, $R_s$, and $R_t$, which may be identical or different, denote hydrogen atoms or $C_{1-3}$-alkyl groups.

Moreover, the saturated alkyl and alkyloxy moieties which contain more than 2 carbon atoms mentioned in the foregoing definitions and those that follow, unless otherwise stated, also include the branched isomers thereof such as, for example, the isopropyl, tert.butyl, isobutyl group, etc.

Preferred compounds of the above general formula I are those wherein $R^1$ denotes a methyl group substituted by a group $R_a$, where
$R_a$ denotes a 3,4-dihydro-quinolinyl group,
a 3,4-dihydro-isoquinolinyl group,
a 1,4-dihydro-quinazolinyl or 4-oxo-1,4-dihydro-quinazolinyl group,
a 3,4-dihydro-quinazolinyl or 4-oxo-3,4-dihydro-quinazolinyl group,
a 1H-benzo[d][1,2]oxazinyl or 1-oxo-1H-benzo[d][1,2]oxazinyl group,
a 4H-benzo[e][1,3]oxazinyl or 4-oxo-4H-benzo[e][1,3]oxazinyl group,
a 4H-benzo[d][1,3]oxazinyl or 4-oxo-4H-benzo[d][1,3]oxazinyl group,
a 2H-benzo[1,4]oxazinyl or 2-oxo-2H-benzo[1,4]oxazinyl group,
a 4H-benzo[e][1,3]thiazinyl or 4-oxo-4H-benzo[e][1,3]thiazinyl group,
a 4H-benzo[d][1,3]thiazinyl or 2H-benzo[1,4]thiazinyl group,
a 2-oxo-2H-benzo[e][1,3]oxazinyl or 2,2-dioxo-1H-benzo[c][1,2]thiazinyl group,
a 2,3-dihydro-1H-benzo[e][1,4]diazepinyl or 2-oxo-2,3-dihydro-1H-benzo[e][1,4]diazepinyl group,
a 4,5-dihydro-3H-benzo[b][1,4]diazepinyl or 4-oxo-4,5-dihydro-3H-benzo[b][1,4]diazepinyl group,
a 5-oxo-4,5-dihydro-3H-benzo[e][1,4]diazepinyl group,
a 2,3-dihydro-benzo[f][1,4]oxazepinyl or 2,3-dihydro-benzo[b][1,4]oxazepinyl group,
a 2,3-dihydro-benzo[f][1,4]thiazepinyl or 2,3-dihydro-benzo[b][1,4]thiazepinyl group,
a 5-oxo-4,5-dihydro-benzo[f][1,3,4]oxadiazepinyl group,
a 11H-dibenzo[b,e]azepinyl or 11-oxo-11H-dibenzo[b,e]azepinyl group,
a 11H-benzo[e]pyrido[3,2-b]azepinyl or a 5H-1,9,10-triaza-dibenzo[a,d]cycloheptenyl group,
a 5H-dibenzo[b,e][1,4]diazepinyl or dibenzo[b,f][1,4]oxazepinyl group,
a dibenzo[b,f][1,4]thiazepinyl, 5-oxo-dibenzo[b,f][1,4]thiazepinyl or 5,5-dioxo-dibenzo[b,f][1,4]thiazepinyl group,
a 5H-dibenzo[a,d]cycloheptenyl or 5H-dibenzo[b,f]azepinyl group,
a phenanthridinyl, benzo[c][1,5]naphthyridinyl, benzo[h][1,6]naphthyridinyl, benzo[c][1,8]naphthyridinyl, benzo[f][1,7]naphthyridinyl or 1,5,9-triaza-phenanthrenyl group,
a 1,2,3,4-tetrahydro-phenanthridinyl, 1,2,3,4,4a,10b-hexahydro-phenanthridinyl, 2,3-dihydro-1H-4-aza-cyclopenta[a]naphthyl or 8,9,10,11-tetrahydro-7H-6-aza-cyclohepta[a]naphthyl group,
a 2,3-dihydro-1H-4-oxa-10-aza-phenanthrenyl or 1-oxo-2,3-dihydro-1H-4-oxa-10-aza-phenanthrenyl group,
a phenanthrenyl, benzo[h]quinolinyl, benzo[f]quinolinyl or benzo[f]quinoxalinyl group,
a 5H-benzo[e]pyrrolo[1,2-a][1,4]diazepinyl, thieno[3,2-b][1,4]benzoxazepinyl, 5H-dibenzo[d,f][1,3]diazepinyl or 5-oxa-7-aza-dibenzo[a,c]cycloheptenyl group,
a naphtho[1,2-d]oxazolyl, naphtho[2,1-d]oxazolyl, naphtho[1,2-d]thiazolyl, naphtho[2,1-d]thiazolyl, naphtho[1,2-d]imidazolyl, naphtho[1,2-b]furanyl or naphtho[2,1-b]furanyl group,
or a furo[3,2-c]isoquinolinyl, pyrazolo[1,5-c]quinazolinyl or 1H-perimidinyl group,
while the benzo groups of the above mentioned radicals $R_a$ are substituted by the groups $R^{10}$ to $R^{13}$ and the alkylene units of the above mentioned groups $R_a$ may be substituted by one or two fluorine atoms or one or two $C_{1-3}$-alkyl or $C_{1-3}$-alkyloxy-carbonyl groups and the imino groups of the above mentioned radicals $R_a$ may be substituted by a $C_{1-3}$-alkyl group and
$R^{10}$ denotes a hydrogen atom,
a fluorine, chlorine, bromine or iodine atom,
a $C_{1-3}$-alkyl or cyclopropyl group,
a hydroxy, $C_{1-3}$-alkyloxy or cyclopropyloxy group,
a nitro, amino, $C_{1-3}$-alkylamino or di-($C_{1-3}$-alkyl)amino group,
a $C_{1-3}$-alkyl-carbonylamino or $C_{1-3}$-alkyl-sulphonylamino group,
a cyano, carboxy, $C_{1-3}$-alkyloxy-carbonyl, aminocarbonyl, $C_{1-3}$-alkyl-aminocarbonyl or di-($C_{1-3}$-alkyl)-aminocarbonyl group,
a mercapto, $C_{1-3}$-alkylsulphanyl, $C_{1-3}$-alkysulphinyl, $C_{1-3}$-alkylsulphonyl or aminosulphonyl group or
a difluoromethyl, trifluoromethyl, difluoromethoxy or trifluoromethoxy group and
$R^{11}$, $R^{12}$ and $R^{13}$, which may be identical or different, in each case represent a hydrogen atom, a fluorine, chlorine or bromine atom, a methyl, trifluoromethyl or methoxy group, R² denotes a hydrogen atom or
a C₁₋₃-alkyl, cyclopropyl, trifluoromethyl, cyanomethyl or 2-cyano-ethyl group, Y denotes a nitrogen atom or a group of formula C—R⁵,
while R⁵ denotes a hydrogen atom or a C₁₋₃-alkyl group, R³ denotes a 2-buten-1-yl or 3-methyl-2-buten-1-yl group,
a 1-buten-1-yl group,
a 2-butyn-1-yl group or
a 1-cyclopenten-1-ylmethyl group
and R⁴ denotes a (3-amino-piperidin-1-yl) group, while, unless otherwise stated, the above mentioned alkyl groups may be straight-chain or branched,
the tautomers, enantiomers, diastereomers, the mixtures thereof and the salts thereof.

Particularly preferred are those compounds of the above general formula I wherein R¹ denotes a methyl group substituted by a group Rₐ, where Rₐ denotes a 3,4-dihydro-quinolin-2-yl group,
a 3,4-dihydro-isoquinolin-1-yl group,
a 1,4-dihydro-quinazolin-2-yl or 4-oxo-1,4-dihydro-quinazolin-2-yl group,
a 3,4-dihydro-quinazolin-2-yl or 4-oxo-3,4-dihydro-quinazolin-2-yl group,
a 1H-benzo[d][1,2]oxazin-4-yl or 1-oxo-1H-benzo[d][1,2]oxazin-4-yl group,
a 4H-benzo[e][1,3]oxazin-2-yl or 4-oxo-4H-benzo[e][1,3]oxazin-2-yl group,
a 4H-benzo[d][1,3]oxazin-2-yl or 4-oxo-4H-benzo[d][1,3]oxazin-2-yl group,
a 2H-benzo[1,4]oxazin-3-yl or 2-oxo-2H-benzo[1,4]oxazin-3-yl group,
a 4H-benzo[e][1,3]thiazin-2-yl or 4-oxo-4H-benzo[e][1,3]thiazin-2-yl group,
a 4H-benzo[d][1,3]thiazin-2-yl or 2H-benzo[1,4]thiazin-3-yl group,
a 2-oxo-2H-benzo[e][1,3]oxazin-4-yl or 2,2-dioxo-1H-benzo[c][1,2]thiazin-4-yl group,
a 2,3-dihydro-1H-benzo[e][1,4]diazepin-5-yl or 2-oxo-2,3-dihydro-1H-benzo[e][1,4]diazepin-5-yl group,
a 4,5-dihydro-3H-benzo[b][1,4]diazepin-2-yl or 4-oxo-4,5-dihydro-3H-benzo[b][1,4]diazepin-2-yl group,
a 5-oxo-4,5-dihydro-3H-benzo[e][1,4]diazepin-2-yl group,
a 2,3-dihydro-benzo[f][1,4]oxazepin-5-yl or 2,3-dihydro-benzo[b][1,4]oxazepin-4-yl group,
a 2,3-dihydro-benzo[f][1,4]thiazepin-5-yl or 2,3-dihydro-benzo[b][1,4]thiazepin-4-yl group,
a 5-oxo-4,5-dihydro-benzo[f][1,3,4]oxadiazepin-2-yl group,
a 11H-dibenzo[b,e]azepin-6-yl or 11-oxo-11H-dibenzo[b,e]azepin-6-yl group,
a 11H-benzo[e]pyrido[3,2-b]azepin-6-yl or a 5H-1,9,10-triaza-dibenzo[a,d]-cyclohepten-11-yl group,
a 5H-dibenzo[b,e][1,4]diazepin-11-yl or dibenzo[b,f][1,4]oxazepin-11-yl group,
a dibenzo[b,f][1,4]thiazepin-11-yl, 5-oxo-dibenzo[b,f][1,4]thiazepin-11-yl or 5,5-dioxo-dibenzo[b,f][1,4]thiazepin-11-yl group,
a 5H-dibenzo[a,d]cyclohepten-10-yl or 5H-dibenzo[b,f]azepin-10-yl group,
a phenanthridin-6-yl, benzo[c][1,5]naphthyridin-6-yl, benzo[h][1,6]naphthyridin-5-yl, benzo[c][1,8]naphthyridin-6-yl, benzo[f][1,7]naphthyridin-5-yl or 1,5,9-triaza-phenanthren-10-yl group,
a 1,2,3,4-tetrahydro-phenanthridin-6-yl, 1,2,3,4,4a,10b-hexahydro-phenanthridin-6-yl, 2,3-dihydro-1H-4-aza-cyclopenta[a]naphth-5-yl or 8,9,10,11-tetrahydro-7H-6-aza-cyclohepta[a]naphth-5-yl group,
a 2,3-dihydro-1H-4-oxa-10-aza-phenanthren-9-yl or 1-oxo-2,3-dihydro-1H-4-oxa-10-aza-phenanthren-9-yl group,
a phenanthren-9-yl, benzo[h]quinolin-6-yl, benzo[f]quinolin-6-yl or benzo[f]quinoxalin-6-yl group,
a 5H-benzo[e]pyrrolo[1,2-a][1,4]diazepin-11-yl, thieno[3,2-b][1,4]benzoxazepin-9-yl, 5H-dibenzo[d,f][1,3]diazepin-6-yl or 5-oxa-7-aza-dibenzo[a,c]cyclohepten-6-yl group,
a naphtho[1,2-d]oxazol-2-yl, naphtho[2,1-d]oxazol-2-yl, naphtho[1,2-d]thiazol-2-yl, naphtho[2,1-d]thiazol-2-yl, naphtho[1,2-d]imidazol-2-yl, naphtho[1,2-b]furan-2-yl or naphtho[2,1-b]furan-2-yl group,
or a furo[3,2-c]isoquinolin-5-yl, pyrazolo[1,5-c]quinazolin-5-yl or 1H-perimidin-2-yl group, while the benzo groups of the above mentioned radicals Rₐ are substituted by the groups R¹⁰ to R¹³ and the alkylene units of the above mentioned groups Rₐ may be substituted by one or two fluorine atoms or one or two methyl groups and the imino groups of the above mentioned radicals Rₐ may be substituted by a methyl group and R¹⁰ denotes a hydrogen atom,
a fluorine, chlorine, bromine or iodine atom,
a methyl or ethyl group,
a hydroxy, methoxy or ethoxy group or
a difluoromethyl, trifluoromethyl, difluoromethoxy, or trifluoromethoxy group and R¹¹, R¹² and R¹³, which may be identical or different, each denote a hydrogen, fluorine, chlorine or bromine atom or a methyl, trifluoromethyl or methoxy group, R² denotes a hydrogen atom or
a methyl, cyanomethyl, trifluoromethyl, ethyl, 2-cyano-ethyl, propyl, cyclopropyl or isopropyl group, Y denotes a nitrogen atom or a group of formula C—R⁵,
while R⁵ denotes a hydrogen atom or a methyl, ethyl, propyl or isopropyl group, R³ denotes a 2-buten-1-yl or 3-methyl-2-buten-1-yl group,
a 1-buten-1-yl group,
a 2-butyn-1-yl group or
a 1-cyclopenten-1-ylmethyl group
and R⁴ denotes a (3-amino-piperidin-1-yl) group, the tautomers, enantiomers, diastereomers, the mixtures thereof and the salts thereof.

Most particularly preferred are those compounds of the above general formula I wherein R¹ denotes a 4-oxo-3,4-dihydro-quinazolin-2-ylmethyl group,
a dibenzo[b,f][1,4]oxazepin-11-ylmethyl group,
a phenanthridin-6-ylmethyl group,
a phenanthren-9-ylmethyl group or
a naphtho[1,2-d]oxazol-2-ylmethyl or naphtho[2,1-d]oxazol-2-ylmethyl group, R² denotes a hydrogen atom or a methyl group,
Y denotes a nitrogen atom,
R³ denotes a 2-butyn-1-yl group
and R⁴ denotes a (3-amino-piperidin-1-yl) group, the tautomers, enantiomers, diastereomers, the mixtures thereof and the salts thereof.

The following compounds of general formula I deserve special mention:

(1) 2-(3-amino-piperidin-1-yl)-3-(2-butyn-1-yl)-5-[(dibenzo[b,f][1,4]oxazepin-11-yl)methyl]-3,5-dihydro-imidazo[4,5-d]pyridazin-4-one

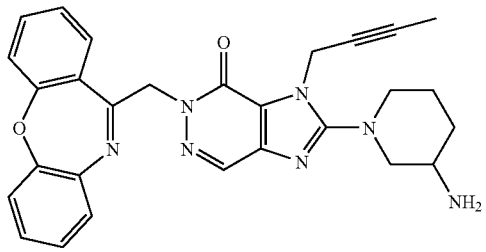

(2) 2-(3-amino-piperidin-1-yl)-3-(2-butyn-1-yl)-5-[(phenanthridin-6-yl)methyl]-3,5-dihydro-imidazo[4,5-d]pyridazin-4-one

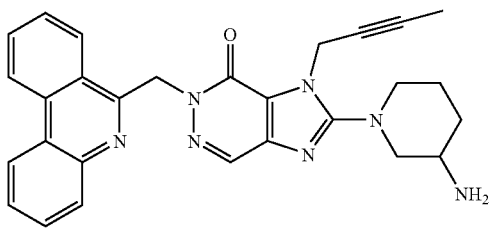

(3) 2-(3-amino-piperidin-1-yl)-3-(2-butyn-1-yl)-5-[(phenanthren-9-yl)methyl]-3,5-dihydro-imidazo[4,5-d]pyridazin-4-one

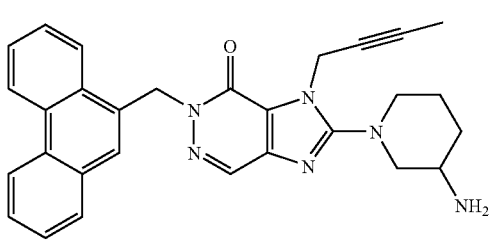

(4) 2-((R)-3-amino-piperidin-1-yl)-3-(2-butyn-1-yl)-5-[(phenanthridin-6-yl)methyl]-7-methyl-3,5-dihydro-imidazo[4,5-d]pyridazin-4-one

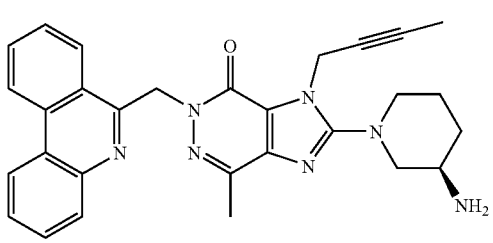

(5) 2-((R)-3-amino-piperidin-1-yl)-3-(2-butyn-1-yl)-5-[(dibenzo[b,f][1,4]oxazepin-11-yl)methyl]-7-methyl-3,5-dihydro-imidazo[4,5-d]pyridazin-4-one

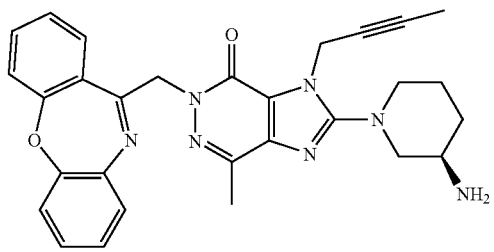

(6) 2-((S)-3-amino-piperidin-1-yl)-3-(2-butyn-1-yl)-5-[(dibenzo[b,f][1,4]oxazepin-11-yl)methyl]-3,5-dihydro-imidazo[4,5-d]pyridazin-4-one

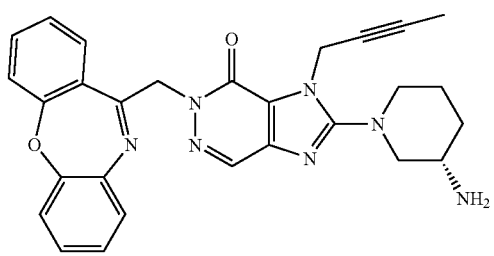

(7) 2-((R)-3-amino-piperidin-1-yl)-3-(2-butyn-1-yl)-5-[(dibenzo[b,f][1,4]oxazepin-11-yl)methyl]-3,5-dihydro-imidazo[4,5-d]pyridazin-4-one

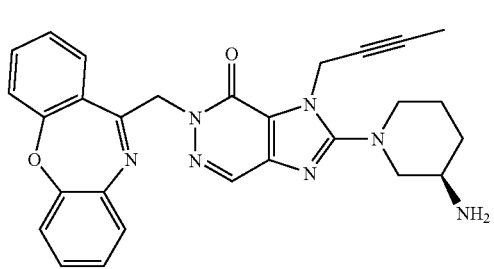

(8) 2-((R)-3-amino-piperidin-1-yl)-3-(2-butyn-1-yl)-5-[(naphtho[2,1-d]oxazol-2-yl)methyl]-3,5-dihydro-imidazo[4,5-d]pyridazin-4-one

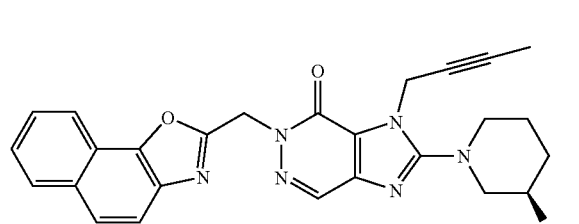

(9) 2-((R)-3-amino-piperidin-1-yl)-3-(2-butyn-1-yl)-5-[(naphtho[1,2-d]oxazol-2-yl)methyl]-3,5-dihydro-imidazo[4,5-d]pyridazin-4-one

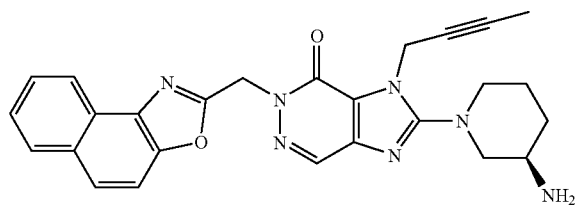

(10) 2-((R)-3-amino-piperidin-1-yl)-3-(2-butyn-1-yl)-5-[(4-oxo-3,4-dihydro-quinazolin-2-yl)methyl]-3,5-dihydro-imidazo[4,5-d]pyridazin-4-one

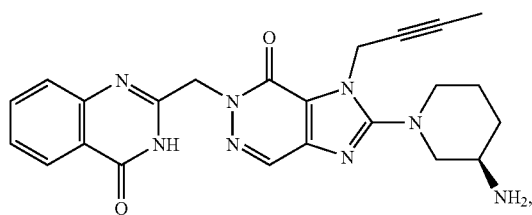

the enantiomers, the mixtures thereof and the salts thereof.
According to the invention the compounds of general formula I are obtained by methods known per se, for example by the following methods:
a) deprotecting a compound of general formula

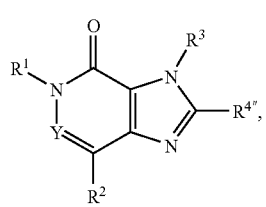

wherein $R^1$, $R^2$, Y and $R^3$ are as hereinbefore defined and $R^{4'''}$ denotes one of the groups mentioned for $R^4$ hereinbefore which contain an imino, amino or alkylamino group, while the imino, amino or alkylamino group is substituted by a protective group.

The liberating of an amino group from a protected precursor is a standard reaction in synthetic organic chemistry. There are many examples of suitable protective groups. A summary of the chemistry of protective groups can be found in Theodora W. Greene and Peter G. M. Wuts, Protective Groups in Organic Synthesis, Second Edition, 1991, published by John Wiley and Sons, and in Philip J. Kocienski, Protecting Groups, published by Georg Thieme, 1994.

The following are examples of protective groups:
the tert.-butyloxycarbonyl group which can be cleaved by treating with an acid such as for example trifluoroacetic acid or hydrochloric acid or by treating with bromotrimethylsilane or iodotrimethylsilane, optionally using a solvent such as methylene chloride, ethyl acetate, dioxane, methanol, isopropanol or diethylether at temperatures between 0° C. and 80° C., the 2,2,2-trichloroethoxycarbonyl group which can be cleaved by treating with metals such as for example zinc or cadmium in a solvent such as acetic acid or a mixture of tetrahydrofuran and a weak aqueous acid at temperatures between 0° C. and the boiling temperature of the solvent used and the carbobenzyloxycarbonyl group which can be cleaved for example by hydrogenolysis in the presence of a noble metal catalyst such as for example palladium-charcoal and a solvent such as for example alcohols, ethyl acetate, dioxane, tetrahydrofuran or mixtures of these solvents at temperatures between 0° C. and the boiling point of the solvent, by treating with boron tribromide in methylene chloride at temperatures between –20° C. and ambient temperature, or by treating with aluminium chloride/anisol at temperatures between 0° C. and ambient temperature.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one stereocentre may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+)- or (–)-menthol and an optically active acyl group in amides, for example, may be a (+)- or (–)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formula II used as starting materials are either known from the literature or may be obtained by methods known from the literature (cf. Examples I to XVI).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in a test set-up in which an extract of human colon carcinoma cell line Caco-2 is used as the DPP IV source. The differentiation of the cells in order to induce the DPP-IV expression was carried out as described by Reiher et al. in an article entitled "Increased expression of intestinal cell line Caco-2", which appeared in Proc. Natl. Acad. Sci. Vol. 90, pages 5757-5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifuging at 35,000 g for 30 minutes at 4° C. (to remove cell debris).

The DPP-IV assay was carried out as follows:

50 μl substrate solution (AFC; AFC is amido-4-trifluoromethylcoumarin), final concentration 100 μM, were placed in black microtitre plates. 20 μl of assay buffer (final concentrations 50 mM Tris HCl pH 7.8, 50 mM NaCl, 1% DMSO) was pipetted in. The reaction was started by adding 30 μl of solubilised Caco-2 protein (final concentration 0.14 μg of protein per well). The test substances to be investigated were typically added prediluted in 20 μl, and the volume of assay buffer was then reduced accordingly. The reaction was carried out at ambient temperature, incubating for 60 minutes. Then the fluorescence was measured in a Victor 1420 Multilabel Counter, the excitation wavelength being 405 nm and the emission wavelength being 535 nm. Blank readings (corresponding to 0% activity) were obtained in mixtures without any Caco-2 protein (volume replaced by assay buffer), control values (corresponding to 100% activity) were obtained in mixtures with no substance added. The potency of the test substances in question, expressed as $IC_{50}$ values, was calculated from dosage/activity curves consisting of 11 measuring points in each case. The following results were obtained:

| Compound (Example No.) | DPP IV inhibition $IC_{50}$ [nM] |
|---|---|
| 1 | 14 |
| 1(1) | 17 |
| 1(2) | 58 |
| 1(3) | 8 |
| 1(4) | 9 |
| 1(7) | 3 |
| 1(8) | 7 |
| 1(9) | 3 |

The compounds prepared according to the invention are well tolerated, as for example when 10 mg/kg of the compound of Example 1 were administered to rats by oral route no changes in the animals' behaviour could be detected.

In view of their ability to inhibit DPP-IV activity, the compounds of general formula I according to the invention and the corresponding pharmaceutically acceptable salts thereof are suitable for treating all those conditions or illnesses which can be influenced by the inhibition of the DPP-IV activity. It is therefore to be expected that the compounds according to the invention will be suitable for the prevention or treatment of diseases or conditions such as type I and type II diabetes mellitus, diabetic complications, metabolic acidosis or ketosis, insulin resistance, dyslipidaemias of various origins, arthritis, atherosclerosis and related diseases, obesity, allograft transplantation and calcitonin-induced osteoporosis. In addition these substances are capable of preventing B-cell degeneration such as e.g. apoptosis or necrosis of pancreatic B-cells. The substances are also suitable for improving or restoring the function of pancreatic cells and also increasing the number and size of pancreatic B-cells. Additionally, and on the basis of the role of the Glucagon-Like Peptides, such as e.g. GLP-1 and GLP-2 and their link with DPP-IV inhibition, it is likely that the compounds according to the invention are suitable for achieving, inter alia, a sedative or anxiety-relieving effect and also of favourably affecting catabolic states after operations or hormonal stress responses or of reducing mortality or morbidity after myocardial infarct. They are also suitable for treating all conditions which are connected with the above mentioned effects and which are mediated by GLP-1 or GLP-2. The compounds according to the invention may also be used as diuretics or antihypertensives and are suitable for preventing and treating acute renal failure. They are also suitable for the prevention and treatment of chronic inflammatory intestinal diseases. It is also expected that DPP-IV inhibitors and hence also the compounds according to the invention may be used to treat infertility or to improve fertility in humans or mammals, particularly when the infertility is connected with insulin resistance or polycystic ovary syndrome. The substances are also suitable for treating deficiencies of growth hormone which are associated with reduced stature.

The compounds according to the invention may also be used in conjunction with other active substances. Therapeutic agents which are suitable for such combinations include, for example, antidiabetics, such as metformin, sulphonylureas (e.g. glibenclamide, tolbutamide, glimepiride), nateglinide, repaglinide, thiazolidinedione (e.g. rosiglitazone, pioglitazone), PPAR-gamma agonists (e.g. GI 262570), alpha-glucosidase inhibitors (e.g. acarbose, voglibose), alpha2 antagonists, insulin and insulin analogues, GLP-1 and GLP-1 analogues (e.g. exendin-4) or amylin. Also, inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, cholesterol absorption inhibitors such as for example ezetimibe, bile acid-binding substances such as for example cholestyramine, HDL-raising compounds such as for example inhibitors of CETP or regulators of ABC1 or active substances for the treatment of obesity, such as e.g. sibutramine or tetrahydrolipostatin, or $β_3$-agonists such as SB-418790 or AD-9677.

It is also possible to combine the compounds with drugs for treating high blood pressure such as e.g. AII antagonists or ACE inhibitors, diuretics, β-blockers, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I

2-[3-(tert.-butyloxycarbonylamino)-piperidin-1-yl]-3-(2-butyn-1-yl)-5-[(dibenzo[b,f][1,4]-oxazepin-11-yl)methyl]-3,5-dihydro-imidazo[4,5-d]pyridazin-4-one 317 mg 11-chloromethyl-dibenzo[b,f][1,4]oxazepin are added to 400 mg 2-[3-(tert.-butyloxycarbonylamino)-piperidin-1-yl]-3-(2-butyn-1-yl)-3,5-dihydro-imidazo[4,5-d]pyridazin-4-one and 276 mg potassium carbonate in 4 ml N,N-dimethylformamide. The reaction mixture is stirred for two hours at 80° C. For working up it is combined with water and the precipitate formed is suction filtered. The crude product is purified by chromatography over a silica gel column with methylene chloride/methanol (100:0 to 70:30) as eluant.

Yield: 120 mg (20% of theory)

Mass spectrum (ESI$^+$): m/z=594 [M+H]$^+$

The following compounds are obtained analogously to Example I:
(1) 2-[3-(tert.-butyloxycarbonylamino)-piperidin-1-yl]-3-(2-butyn-1-yl)-5-[(phenanthridin-6-yl)methyl]-3,5-dihydro-imidazo[4,5-d]pyridazin-4-one
(2) 2-[3-(tert.-butyloxycarbonylamino)-piperidin-1-yl]-3-(2-butyn-1-yl)-5-[(phenanthren-9-yl)methyl]-3,5-dihydro-imidazo[4,5-d]pyridazin-4-one
(3) 2-[(R)-3-(tert.-butyloxycarbonylamino)-piperidin-1-yl]-3-(2-butyn-1-yl)-5-[(phenanthridin-6-yl)methyl]-7-methyl-3,5-dihydro-imidazo[4,5-d]pyridazin-4-one
R$_f$ value: 0.41 (silica gel, cyclohexane/ethyl acetate=3:7)
Mass spectrum (ESI$^+$): m/z=592 [M+H]$^+$
(4) 2-[(R)-3-(tert.-butyloxycarbonylamino)-piperidin-1-yl]-3-(2-butyn-1-yl)-5-[(dibenzo[b,f][1,4]oxazepin-11-yl)methyl]-7-methyl-3,5-dihydro-imidazo[4,5-d]pyridazin-4-one
R$_f$ value: 0.50 (silica gel, cyclohexane/ethyl acetate=2:8)
Mass spectrum (ESI$^+$): m/z=608 [M+H]$^+$
(5) 2-bromo-3-(2-butyn-1-yl)-5-[(dibenzo[b,f][1,4]oxazepin-11-yl)methyl]-3,5-dihydro-imidazo[4,5-d]pyridazin-4-one
Mass spectrum (ESI$^+$): m/z=474, 476 [M+H]$^+$
(6) 2-bromo-3-(2-butyn-1-yl)-5-[(naphtho[2,1-d]oxazol-2-yl)methyl]-3,5-dihydro-imidazo[4,5-d]pyridazin-4-one
R$_f$ value: 0.80 (silica gel, methylene chloride/ethanol=9:1)
(7) 2-bromo-3-(2-butyn-1-yl)-5-[(naphtho[1,2-d]oxazol-2-yl)methyl]-3,5-dihydro-imidazo[4,5-d]pyridazin-4-one
R$_f$ value: 0.50 (silica gel, methylene chloride/methanol=19:1)
(8) 2-[(R)-3-(tert.-butyloxycarbonylamino)-piperidin-1-yl]-3-(2-butyn-1-yl)-5-cyanomethyl-3,5-dihydro-imidazo[4,5-d]pyridazin-4-one
R$_f$ value: 0.40 (silica gel, petroleum ether/ethyl acetate=1:4)
Mass spectrum (ESI$^+$): m/z=426 [M+H]$^+$

EXAMPLE II

2-[3-(tert.-butyloxycarbonylamino)-piperidin-1-yl]-3-(2-butyn-1-yl)-3,5-dihydro-imidazo[4,5-d]pyridazin-4-one 2.50 g 3-(tert.-butyloxycarbonylamino)-piperidine are added to 2.65 g 2-bromo-3-(2-butyn-1-yl)-3,5-dihydro-imidazo[4,5-d]pyridazin-4-one and 2.12 g sodium carbonate in 5 ml dimethylsulphoxide. The reaction mixture is stirred overnight at 85° C.

After cooling to ambient temperature it is combined with water and extracted with ethyl acetate. The combined organic phases are dried over magnesium carbonate and evaporated down. The crude product is further reacted without any further purification.

Mass spectrum (ESI$^+$): m/z=387 [M+H]$^+$

The following compounds are obtained analogously to Example II:
(1) 2-[(R)-3-(tert.-butyloxycarbonylamino)-piperidin-1-yl]-3-(2-butyn-1-yl)-7-methyl-3,5-dihydro-imidazo[4,5-d]pyridazin-4-one
R$_f$ value: 0.15 (silica gel, cyclohexane/ethyl acetate=3:7)
Mass spectrum (ESI$^+$): m/z=401 [M+H]$^+$
(2) 2-[(S)-3-(tert.-butyloxycarbonylamino)-piperidin-1-yl]-3-(2-butyn-1-yl)-5-[(dibenzo[b,f][1,4]oxazepin-11-yl)methyl]-3,5-dihydro-imidazo[4,5-d]pyridazin-4-one
Mass spectrum (ESI$^+$): m/z=594 [M+H]$^+$
(3) 2-[(R)-3-(tert.-butyloxycarbonylamino)-piperidin-1-yl]-3-(2-butyn-1-yl)-5-[(dibenzo[b,f][1,4]oxazepin-11-yl)methyl]-3,5-dihydro-imidazo[4,5-d]pyridazin-4-one
Mass spectrum (ESI$^+$): m/z=594 [M+H]$^+$
(4) 2-[(R)-3-(tert.-butyloxycarbonylamino)-piperidin-1-yl]-3-(2-butyn-1-yl)-5-[(naphtho[2,1-d]oxazol-2-yl)methyl]-3,5-dihydro-imidazo[4,5-d]pyridazin-4-one
R$_f$ value: 0.70 (silica gel, methylene chloride/ethanol=9:1)
(5) 2-[(R)-3-(tert.-butyloxycarbonylamino)-piperidin-1-yl]-3-(2-butyn-1-yl)-5-[(naphtho[1,2-d]oxazol-2-yl)methyl]-3,5-dihydro-imidazo[4,5-d]pyridazin-4-one
R$_f$ value: 0.65 (silica gel, methylene chloride/methanol=9:1)
Mass spectrum (ESI$^+$): m/z=568 [M+H]$^+$
(6) 2-[(R)-3-(tert.-butyloxycarbonylamino)-piperidin-1-yl]-3-(2-butyn-1-yl)-3,5-dihydro-imidazo[4,5-d]pyridazin-4-one
Mass spectrum (ESI$^+$): m/z=387 [M+H]$^+$
R$_f$ value: 0.50 (silica gel, methylene chloride/ethanol=9:1)

EXAMPLE III 2-bromo-3-(2-butyn-1-yl)-3,5-dihydro-imidazo[4,5-d]pyridazin-4-one 0.63 ml hydrazine hydrate are added dropwise to 3.68 g methyl 2-bromo-3-(2-butyn-1-yl)-5-formyl-3H-imidazole-4-carboxylate in 50 ml of ethanol. The reaction mixture is stirred for one hour at ambient temperature, then 3 ml acetic acid are added and the reaction mixture is refluxed for a further hour. The precipitate formed is suction filtered, washed with ethanol and diethyl ether and dried.

Yield: 2.65 g (77% of theory)
Mass spectrum (ESI+): m/z=267, 269 [M+H]+

EXAMPLE IV methyl 2-bromo-3-(2-butyn-1-yl)-5-formyl-3H-imidazole-4-carboxylate 45 ml diisobutylaluminum hydride solution (1M in toluene) are added dropwise to 12.45 g dimethyl 2-bromo-3-(2-butyn-1-yl)-1H-imidazole-4,5-dicarboxylate in 150 ml of tetrahydrofuran under an argon atmosphere at −65° C. The reaction mixture is stirred for two hours at −65° C., then another 9 ml diisobutylaluminum hydride solution are added. After another hour the reaction mixture is quenched at −65° C. with a mixture of 1 M hydrochloric acid and tetrahydrofuran (1:1) and stirred for ten minutes. Then the cooling bath is removed, the reaction mixture is diluted with water and extracted with ethyl acetate. The combined organic phases are dried over magnesium sulphate and evaporated down. The crude product is purified by chromatography over a silica gel column with cyclohexane/ethyl acetate (2:1 to 1:1).
Yield: 9.58 g (85% of theory)
Mass spectrum (ESI+): m/z=285, 287 [M+H]+
The following compounds are obtained analogously to Example IV:
(1) methyl 2-bromo-3-(3-methyl-2-buten-1-yl)-5-formyl-3H-imidazole-4-carboxylate
Mass spectrum (ESI+): m/z=301, 303 [M+H]+

EXAMPLE V dimethyl 2-bromo-3-(2-butyn-1-yl)-1H-imidazole-4,5-dicarboxylate 4.53 ml of 1-bromo-2-butyne are added to 13.20 g dimethyl 2-bromo-1H-imidazole-4,5-dicarboxylate and 8.57 g potassium carbonate in 70 ml N,N-dimethylformamide and the reaction mixture is stirred overnight at ambient temperature.
For working up it is combined with water and extracted with ethyl acetate. The combined organic phases are dried over magnesium sulphate and evaporated down.
Yield: 14.58 g (92% of theory)
Mass spectrum (ESI+): m/z=315, 317 [M+H]+
The following compounds are obtained analogously to Example V:
(1) dimethyl 2-bromo-3-(3-methyl-2-buten-1-yl)-1H-imidazole-4,5-dicarboxylate
Mass spectrum (ESI+): m/z=331, 333 [M+H]+

EXAMPLE VI

Dimethyl 2-bromo-1H-imidazole-4,5-dicarboxylate 6.11 ml bromine are added to 19.80 g dimethyl 1H-imidazole-4,5-dicarboxylate and 14.92 g potassium carbonate in 600 ml methylene chloride. The reaction mixture is stirred for one hour at ambient temperature, then a mixture of saturated sodium sulphite solution and saturated sodium chloride solution (1:1) is added. The organic phase is largely separated off and the aqueous phase is extracted with ethyl acetate several times. The combined organic phases are dried over magnesium sulphate and evaporated down, leaving about 7.40 g crude product. The aqueous phase is combined with ethyl acetate and extracted overnight in an extraction apparatus. The ethyl acetate extract is evaporated down and the flask residue is combined with the crude product already obtained.

Yield: 13.10 g (46% of theory)
Mass spectrum (ESI+): m/z=263, 265 [M+H]+

EXAMPLE VII

2-Bromo-3-(2-butyn-1-yl)-7-methyl-3,5-dihydro-imidazo[4,5-d]pyridazin-4-one 0.50 ml of 1-bromo-2-butyne are added to 1.30 g 2-bromo-7-methyl-3,5-dihydro-imidazo[4,5-d]pyridazin-4-one and 0.99 ml Hünig base in 30 ml of N,N-dimethylformamide. The reaction mixture is stirred for three hours at ambient temperature. Then the solvent is distilled off in vacuo using the rotary evaporator. The flask residue is stirred with 40 ml of water and 0.5 ml concentrated aqueous ammonia solution, suction filtered and washed with ethanol as well as diethyl ether.
Yield: 1.30 g (82% of theory)
$R_f$ value: 0.60 (silica gel, cyclohexane/ethyl acetate=3:7)
Mass spectrum (ESI+): m/z=281, 283 [M+H]+

EXAMPLE VIII 2-bromo-7-methyl-3,5-dihydro-imidazo[4,5-d]pyridazin-4-one 5.20 ml of a 1.8 M solution of bromine in acetonitrile are slowly added dropwise to 1.40 g of 7-methyl-3,5-dihydro-imidazo[4,5-d]pyridazin-4-one and 1.30 g potassium carbonate in 40 ml acetonitrile. Then the reaction mixture is heated to 70° C., whereupon the mixture is rapidly decolourised. More bromine solution and potassium carbonate are added batchwise until the reaction has ended, according to HPLC-MS. For working up the reaction mixture is evaporated down, stirred with 100 ml of water and suction filtered. The filtrate is acidified with 1 M hydrochloric acid and extracted with ethyl acetate. The combined extracts are dried over sodium sulphate and evaporated down.
Yield: 1.30 g (61% of theory)
$R_f$ value: 0.37 (silica gel, methylene chloride/methanol=9:1)
Mass spectrum (ESI+): m/z=229, 231 [M+H]+

EXAMPLE IX 7-methyl-3,5-dihydro-imidazo[4,5-d]pyridazin-4-one

A solution of 4.00 g sodium nitrite in 15 ml of water is added dropwise at 50° C. to 2.20 g of 4-amino-7-methyl-3H-imidazo[4,5-d]pyridazine in a mixture of 30 ml acetic acid, 5 ml of water and 0.5 ml concentrated sulphuric acid. The reaction mixture is stirred for a further two hours at 50° C. and then heated to 90° C. for one hour. After cooling to ambient temperature the reaction mixture is diluted with 30 ml of water. The precipitate formed is suction filtered, washed with water, ethanol and diethyl ether and dried.
Yield: 1.00 g (45% of theory)
Mass spectrum (ESI+): m/z=151 [M+H]+

EXAMPLE X 4-amino-7-methyl-3H-imidazo[4,5-d]pyridazine

A mixture of 2.00 g 5-acetyl-3H-imidazole-4-carbonitrile and 4.00 ml hydrazine hydrate in 50 ml of ethanol is heated to 100° C., until the reaction is complete according to HPLC-MS. After cooling to ambient temperature the reaction mixture is evaporated down, stirred with 20 ml of cold ethanol and suction filtered. The filter cake is washed with diethyl ether and dried.

Yield: 2.10 g (95% of theory)
Mass spectrum (ESI$^+$): m/z=150 [M+H]$^+$

EXAMPLE XI 5-acetyl-3H-imidazole-4-carbonitrile 57 ml of a 3 M solution of methylmagnesium bromide in diethyl ether are added to 7.00 g of 4,5-dicyano-imidazole in 80 ml of tetrahydrofuran under an argon atmosphere, while the temperature is maintained between 5° C. and 15° C.

After two hours the reaction is complete according to thin layer chromatography and the reaction mixture is diluted with 400 ml of ethyl acetate. Then 400 ml saturated ammonium chloride solution are slowly added. After ten minutes the mixture is acidified with semiconcentrated sulphuric acid and stirred for another twenty minutes before the organic phase is separated off. The aqueous phase is extracted with ethyl acetate and the combined organic phases are dried over sodium sulphate and evaporated down. The flask residue is stirred with ethyl acetate, suction filtered and washed with ethyl acetate and diethyl ether.

Yield: 3.30 g (43% of theory)
Mass spectrum (ESI$^+$): m/z=136 [M+H]$^+$

EXAMPLE XII 2-chloromethyl-naphtho[2,1-d]oxazole

Prepared by reacting 2.93 g of 2-amino-1-naphthol with 3.54 g of 2-chloro-1,1,1-triethoxy-ethane in 25 ml of ethanol at 60° C.

Yield: 1.90 g (58% of theory)
$R_f$ value: 0.55 (silica gel, petroleum ether/ethyl acetate=9:1)
Mass spectrum (ESI$^+$): m/z=218, 220 [M+H]$^+$ The following compounds are obtained analogously to Example XII:
(1) 2-chloromethyl-naphtho[1,2-d]oxazole
$R_f$ value: 0.90 (silica gel, methylene chloride/methanol=19:1)
Mass spectrum (ESI$^+$): m/z=218, 220 [M+H]$^+$

EXAMPLE XIII 2-bromo-3-(3-methyl-2-buten-1-yl)-3,5-dihydro-imidazo[4,5-c]pyridin-4-one 1.55 g Burgess reagent (methoxycarbonylsulphamoyl-triethylammonium-N-betaine) are added to 1.60 g of 2-bromo-7-hydroxy-3-(3-methyl-2-buten-1-yl)-3,5,6,7-tetrahydro-imidazo[4,5-c]pyridin-4-one in 20 ml methylene chloride and 4 ml of tetrahydrofuran. The reaction mixture is stirred for eight hours at 60° C., then another 0.3 equivalents Burgess reagent is added. After a further two hours the cooled reaction mixture is combined with aqueous sodium hydrogen carbonate solution and extracted with ethyl acetate. The combined organic phases are dried over magnesium sulphate and evaporated down. The flask residue is chromatographed through a silica gel column with methylene chloride/methanol (1:0 to 10:1) as eluant.

Yield: 1.06 g (60% of theory)
Mass spectrum (ESI$^+$): m/z=282, 284 [M+H]$^+$

EXAMPLE XIV 2-bromo-7-hydroxy-3-(3-methyl-2-buten-1-yl)-3,5,6,7-tetrahydro-imidazo[4,5-c]pyridin-4-one 90 ml of water and 5.40 g iron powder are added to 4.15 g methyl 2-bromo-5-(1-hydroxy-2-nitro-ethyl)-3-(3-methyl-2-buten-1-yl)-3H-imidazole-4-carboxylate in 270 ml of ethanol. The mixture is refluxed, combined with 36 ml glacial acetic acid and stirred for one and a half hours at reflux temperature. The cooled reaction solution is filtered through Celite. The filtrate is evaporated down, combined with ethanol and made basic with solid potassium carbonate. The mixture is stirred for three hours at 60° C. Then the ethanol is distilled off, the flask residue is combined with water and extracted with ethyl acetate. The combined extracts are dried over magnesium sulphate and evaporated down. The crude product is purified by chromatography over a silica gel column with methylene chloride/methanol (1:1 to 7:1) as eluant.

Yield: 1.62 g (47% of theory)
Mass spectrum (ESI$^+$): m/z=300, 302 [M+H]$^+$

EXAMPLE XV

Methyl 2-bromo-5-(1-hydroxy-2-nitro-ethyl)-3-(3-methyl-2-buten-1-yl)-3H-imidazole-4-carboxylate 35 ml nitromethane are added to 1.14 g caesium carbonate in 15 ml of methanol at ambient temperature. Then the mixture is combined with a solution of 3.50 g methyl 2-bromo-3-(3-methyl-2-buten-1-yl)-5-formyl-3H-imidazole-4-carboxylate in 20 ml of methanol and 5 ml methylene chloride and stirred for 15 minutes at ambient temperature. Then 0.5 ml acetic acid are added and the solution is evaporated down in vacuo. The flask residue is combined with aqueous sodium hydrogen carbonate solution and extracted with ethyl acetate. The combined organic phases are dried over magnesium sulphate and evaporated down.

Yield: 4.15 g (99% of theory)
Mass spectrum (ESI$^+$): m/z=362, 364 [M+H]$^+$

EXAMPLE XVI

2-[(R)-3-(tert.-butyloxycarbonylamino)-piperidin-1-yl]-3-(2-butyn-1-yl)-5-[(4-oxo-3,4-dihydro-quinazolin-2-yl)methyl]-3,5-dihydro-imidazo[4,5-d]pyridazin-4-one 40 mg sodium methoxide (95%) are added to a solution of 605 mg 2-[(R)-3-(tert.-butyloxycarbonylamino)-piperidin-1-yl]-3-(2-butyn-1-yl)-5-cyanomethyl-3,5-dihydro-imidazo[4,5-d]pyridazin-4-one in 9 ml of methanol. The mixture is stirred for one hour at ambient temperature and then neutralised with 41 µL glacial acetic acid. Then a solution of 195 mg anthranilic acid in 2 ml of methanol is added and the reaction mixture is heated to 70° C. After about two hours a white, voluminous precipitate is formed and the reaction mixture is cooled to ambient temperature. The precipitate formed is suction filtered, washed with cold methanol and dried.

Yield: 234 mg (30% of theory)
Mass spectrum (ESI$^+$): m/z=545 [M+H]$^+$

Preparation of the final compounds:

EXAMPLE 1

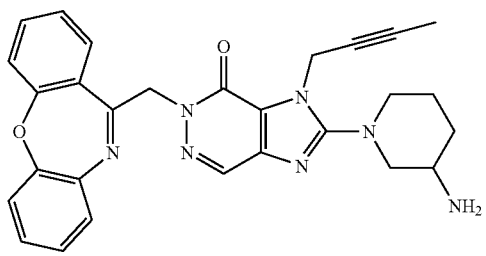

2-(3-amino-piperidin-1-yl)-3-(2-butyn-1-yl)-5-[(dibenzo[b,f][1,4]oxazepin-11-yl)methyl]-3,5-dihydro-imidazo[4,5-d]pyridazin-4-one 0.33 ml trifluoroacetic acid are added to 120 mg 2-[3-(tert.-butyloxycarbonylamino)-piperidin-1-yl]-3-(2-butyn-1-yl)-5-[(dibenzo[b,f][1,4]oxazepin-11-yl)methyl]-3,5-dihydro-imidazo[4,5-d]pyridazin-4-one in 3 ml methylene chloride while cooling with an ice bath. The reaction mixture is stirred overnight at ambient temperature.

For working up it is poured onto cooled saturated potassium carbonate solution and extracted with methylene chloride. The organic phase is separated off and evaporated down. The crude product is purified by chromatography over a silica gel column with methylene chloride/methanol (100:0 to 70:30) as eluant.

Yield: 63 mg (63% of theory)
Mass spectrum (ESI$^+$): m/z=494 [M+H]$^+$

The following compounds are obtained analogously to Example 1:

(1) 2-(3-amino-piperidin-1-yl)-3-(2-butyn-1-yl)-5-[(phenanthridin-6-yl)methyl]-3,5-dihydro-imidazo[4,5-d]pyridazin-4-one

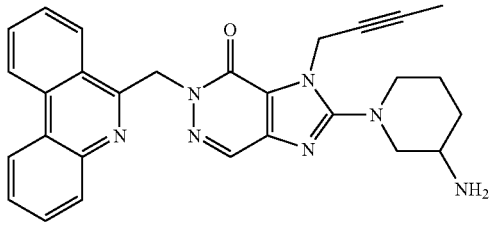

Mass spectrum (ESI$^+$): m/z=478 [M+H]$^+$ (2) 2-(3-amino-piperidin-1-yl)-3-(2-butyn-1-yl)-5-[(phenanthren-9-yl)methyl]-3,5-dihydro-imidazo[4,5-d]pyridazin-4-one

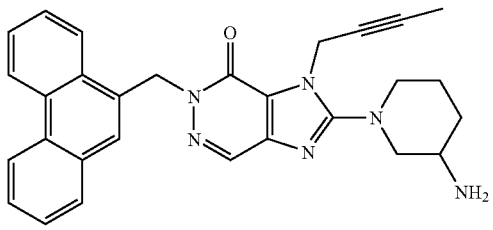

Mass spectrum (ESI$^+$): m/z=477 [M+H]$^+$ (3) 2-((R)-3-amino-piperidin-1-yl)-3-(2-butyn-1-yl)-5-[(phenanthridin-6-yl)methyl]-7-methyl-3,5-dihydro-imidazo[4,5-d]pyridazin-4-one x trifluoroacetic acid

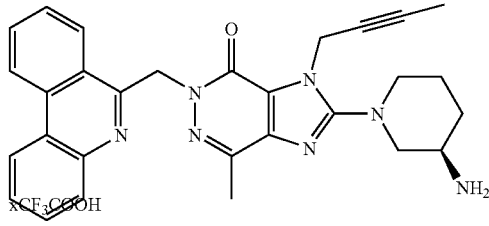

R$_f$ value: 0.45 (Reversed phase ready-made TLC plate (E. Merck), acetonitrile/water/trifluoroacetic acid=50:50:0.1)
Mass spectrum (ESI$^+$): m/z=492 [M+H]$^+$ (4) 2-((R)-3-amino-piperidin-1-yl)-3-(2-butyn-1-yl)-5-[(dibenzo[b,f][1,4]oxazepin-11-yl)methyl]-7-methyl-3,5-dihydro-imidazo[4,5-d]pyridazin-4-one

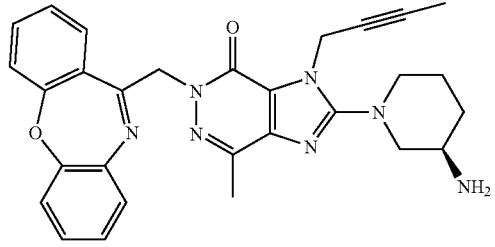

Carried out with isopropanolic hydrochloric acid (5-6 M) in methylene chloride.
Mass spectrum (ESI$^+$): m/z=508 [M+H]$^+$ (5) 2-((S)-3-amino-piperidin-1-yl)-3-(2-butyn-1-yl)-5-[(dibenzo[b,f][1,4]oxazepin-11-yl)methyl]-3,5-dihydro-imidazo[4,5-d]pyridazin-4-one

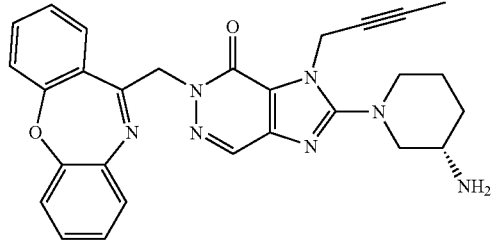

Mass spectrum (ESI$^+$): m/z=494 [M+H]$^+$ (6) 2-((R)-3-amino-piperidin-1-yl)-3-(2-butyn-1-yl)-5-[(dibenzo[b,f][1,4]oxazepin-11-yl)methyl]-3,5-dihydro-imidazo[4,5-d]pyridazin-4-one

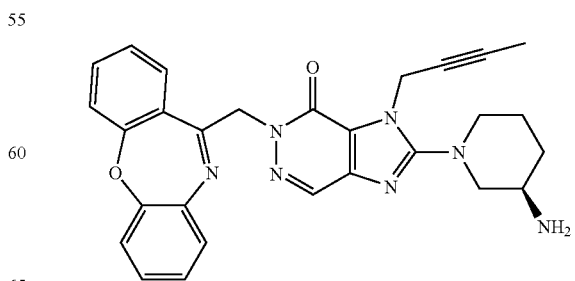

Mass spectrum (ESI$^+$): m/z=494 [M+H]$^+$ (7) 2-((R)-3-amino-piperidin-1-yl)-3-(2-butyn-1-yl)-5-[(naphtho[2,1-d]oxazol-2-yl)methyl]-3,5-dihydro-imidazo[4,5-d]pyridazin-4-one

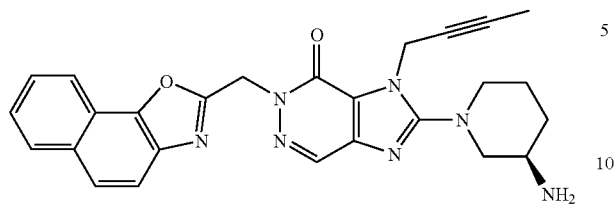

R$_f$ value: 0.40 (silica gel, methylene chloride/ethanol/conc. aqueous ammonia=90:10:2)
Mass spectrum (ESI$^+$): m/z=468 [M+H]$^+$ (8) 2-((R)-3-amino-piperidin-1-yl)-3-(2-butyn-1-yl)-5-[(naphtho[1,2-d]oxazol-2-yl)methyl]-3,5-dihydro-imidazo[4,5-d]pyridazin-4-one

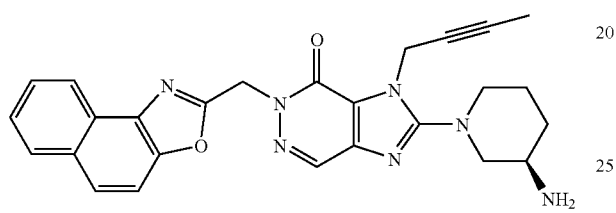

Mass spectrum (ESI$^+$): m/z=468 [M+H]$^+$ (9) 2-((R)-3-amino-piperidin-1-yl)-3-(2-butyn-1-yl)-5-[(4-oxo-3,4-dihydro-quinazolin-2-yl)methyl]-3,5-dihydro-imidazo[4,5-d]pyridazin-4-one

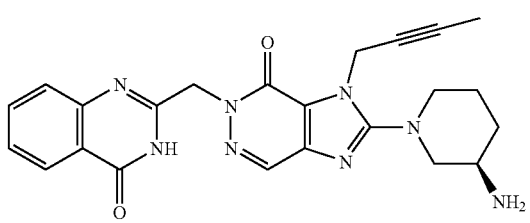

Mass spectrum (ESI$^+$): m/z=445 [M+H]$^+$

The following compounds may also be obtained analogously to the foregoing Examples and other methods known from the literature:

| No. | Name | Structural formula |
|---|---|---|
| (1) | 2-(3-amino-piperidin-1-yl)-3-(2-buten-1-yl)-5-[(3,4-dihydro-quinolin-2-yl)methyl]-6,7-dimethyl-3,5-dihydro-imidazo[4,5-c]pyridin-4-one | |
| (2) | 2-(3-amino-piperidin-1-yl)-3-(2-butyn-1-yl)-5-[(3,4-dihydro-isoquinolin-1-yl)methyl]-7-cyclopropyl-3,5-dihydro-imidazo[4,5-d]pyridazin-4-one | |
| (3) | 2-(3-amino-piperidin-1-yl)-3-(2-butyn-1-yl)-5-[(3,3-dimethyl-3,4-dihydro-isoquinolin-1-yl)methyl]-3,5-dihydro-imidazo[4,5-d]pyridazin-4-one | |

-continued

| No. | Name | Structural formula |
|---|---|---|
| (4) | 2-(3-amino-piperidin-1-yl)-3-(2-butyn-1-yl)-5-[(4,4-dimethyl-3,4-dihydro-isoquinolin-1-yl)methyl]-3,5-dihydro-imidazo[4,5-d]pyridazin-4-one | 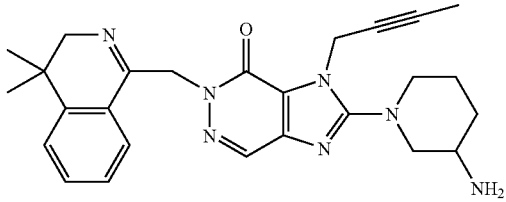 |
| (5) | 2-(3-amino-piperidin-1-yl)-3-(2-butyn-1-yl)-5-[(1-methyl-1,4-dihydro-quinazolin-2-yl)methyl]-3,5-dihydro-imidazo[4,5-d]pyridazin-4-one | 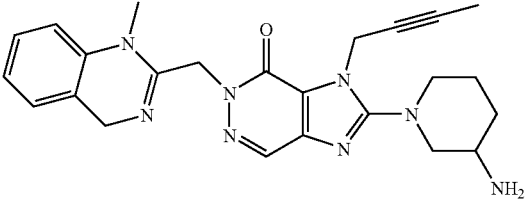 |
| (6) | 2-(3-amino-piperidin-1-yl)-3-(2-butyn-1-yl)-5-[(1-methyl-4-oxo-1,4-dihydro-quinazolin-2-yl)methyl]3,5-dihydro-imidazo[4,5-d]pyridazin-4-one | 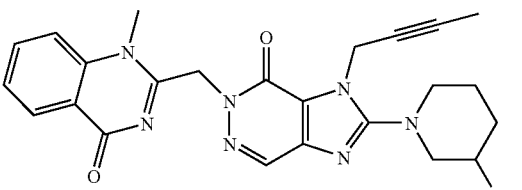 |
| (7) | 2-(3-amino-piperidin-1-yl)-3-(2-buten-1-yl)-5-[(5,6,7,8-tetrafluoro-1-methyl-1,4-dihydro-quinazolin-2-yl)methyl]-3,5-dihydro-imidazo[4,5-c]pyridin-4-one | 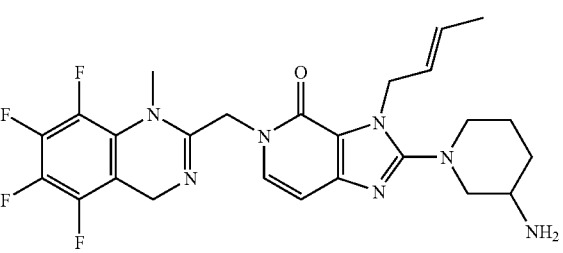 |
| (8) | 2-(3-amino-piperidin-1-yl)-3-(2-buten-1-yl)-5-[(3,4-dihydro-quinazolin-2-yl)methyl]-3,5-dihydro-imidazo[4,5-d]pyridazin-4-one | 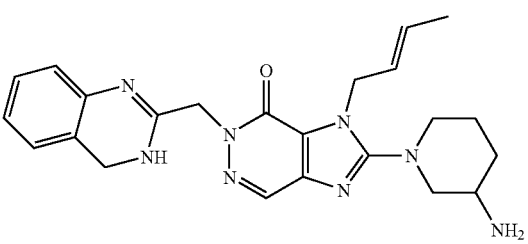 |
| (9) | 2-(3-amino-piperidin-1-yl)-3-(2-butyn-1-yl)-5-[(3-methyl-3,4-dihydro-quinazolin-2-yl)methyl]-3,5-dihydro-imidazo[4,5-d]pyridazin-4-one | 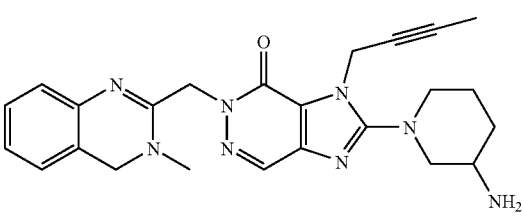 |
| (10) | 2-(3-amino-piperidin-1-yl)-3-(2-butyn-1-yl)-5-[(3-methyl-3,4-dihydro-quinazolin-2-yl)methyl]-3,5-dihydro-imidazo[4,5-d]pyridin-4-one | 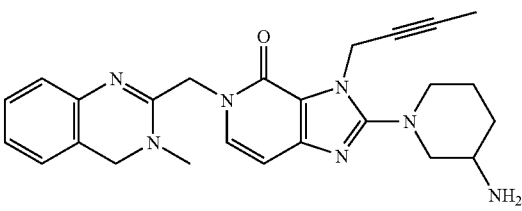 |

-continued

| No. | Name | Structural formula |
|---|---|---|
| (11) | 2-(3-amino-piperidin-1-yl)-3-(1-buten-1-yl)-5-[(1H-benzo[d][1,2]oxazin-4-yl)methyl]-3,5-dihydro-imidazo[4,5-d]pyridazin-4-one | |
| (12) | 2-(3-amino-piperidin-1-yl)-3-(2-butyn-1-yl)-5-[(1-oxo-1H-benzo[d][1,2]oxazin-4-yl)methyl]-3,5-dihydro-imidazo[4,5-d]pyridazin-4-one | |
| (13) | 2-(3-amino-piperidin-1-yl)-3-(2-butyn-1-yl)-5-[(4H-benzo[e][1,3]oxazin-2-yl)methyl]-3,5-dihydro-imidazo[4,5-d]pyridazin-4-one | |
| (14) | 2-(3-amino-piperidin-1-yl)-3-(2-buten-1-yl)-5-[(4,4-dimethyl-4H-benzo[e][1,3]oxazin-2-yl)methyl]-3,5-dihydro-imidazo[4,5-d]pyridazin-4-one | |
| (15) | 2-(3-amino-piperidin-1-yl)-3-(2-butyn-1-yl)-5-[(4-oxo-4H-benzo[e][1,3]oxazin-2-yl)methyl]-3,5-dihydro-imidazo[4,5-d]pyridazin-4-one | |
| (16) | 2-(3-amino-piperidin-1-yl)-3-(2-butyn-1-yl)-5-[(4H-benzo[d][1,3]oxazin-2-yl)methyl]-3,5-dihydro-imidazo[4,5-d]pyridazin-4-one | |
| (17) | 2-(3-amino-piperidin-1-yl)-3-(2-butyn-1-yl)-5-[(4H-benzo[d][1,3]oxazin-2-yl)methyl]-7-methyl-3,5-dihydro-imidazo[4,5-c]pyridin-4-one | |

-continued

| No. | Name | Structural formula |
|---|---|---|
| (19) | 2-(3-amino-piperidin-1-yl)-3-(2-butyn-1-yl)-5-[(4,4-dimethyl-4H-benzo[d][1,3]oxazin-2-yl)methyl]-3,5-dihydro-imidazo[4,5-d]pyridazin-4-one | 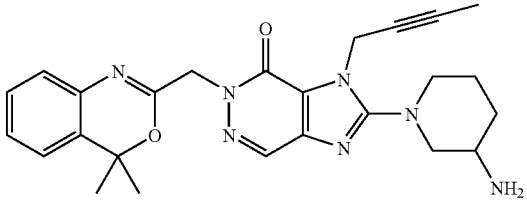 |
| (20) | 2-(3-amino-piperidin-1-yl)-3-(2-butyn-1-yl)-5-[(4-oxo-4H-benzo[d][1,3]oxazin-2-yl)methyl]-3,5-dihydro-imidazo[4,5-d]pyridazin-4-one | 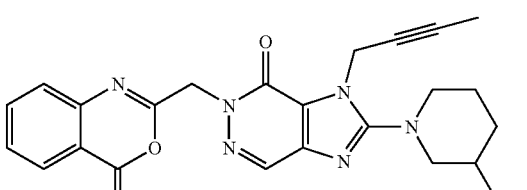 |
| (21) | 2-(3-amino-piperidin-1-yl)-3-(2-butyn-1-yl)-5-[(2H-benzo[1,4]oxazin-3-yl)methyl]-3,5-dihydro-imidazo[4,5-d]pyridazin-4-one | 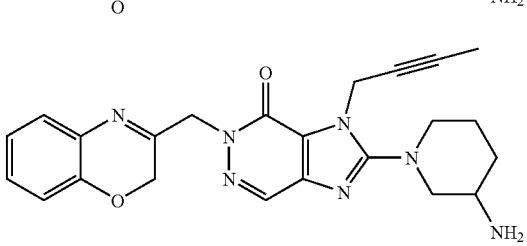 |
| (22) | 2-(3-amino-piperidin-1-yl)-3-(2-butyn-1-yl)-5-[(2-oxo-2H-benzo[1,4]oxazin-3-yl)methyl]-3,5-dihydro-imidazo[4,5-d]pyridazin-4-one | 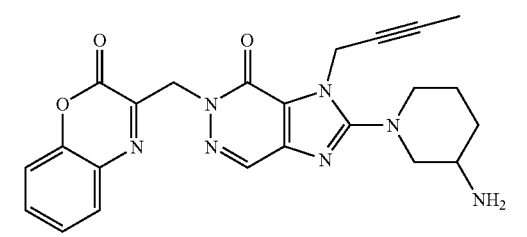 |
| (23) | 2-(3-amino-piperidin-1-yl)-3-(2-butyn-1-yl)-5-[(2,2-dimethyl-2H-benzo[1,4]oxazin-3-yl)methyl]-3,5-dihydro-imidazo[4,5-d]pyridazin-4-one | 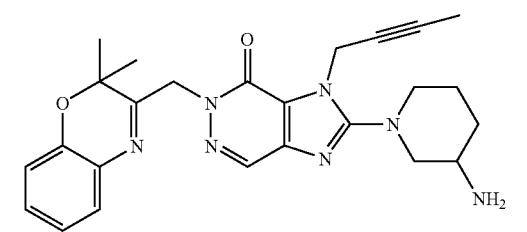 |
| (24) | 2-(3-amino-piperidin-1-yl)-3-(2-butyn-1-yl)-5-[4H-benzo[e][1,3]thiazin-2-yl)methyl]-3,5-dihydro-imidazo[4,5-d]pyridazin-4-one | 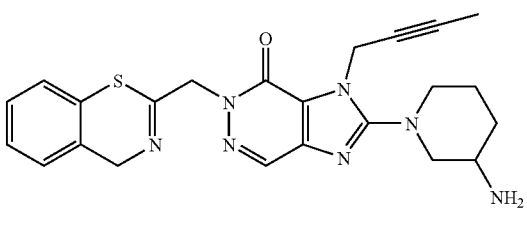 |
| (25) | 2-(3-amino-piperidin-1-yl)-3-(2-butyn-1-yl)-5-[4,4-dimethyl-4H-benzo[e][1,3]thiazin-2-yl)methyl]-3,5-dihydro-imidazo[4,5-d]pyridazin-4-one | 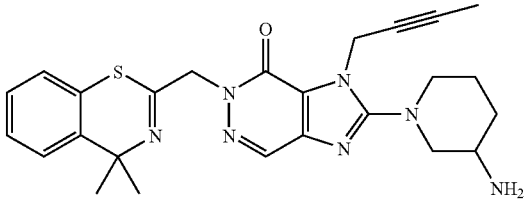 |

-continued

| No. | Name | Structural formula |
|---|---|---|
| (26) | 2-(3-amino-piperidin-1-yl)-3-(2-butyn-1-yl)-5-[4-oxo-4H-benzo[e][1,3]thiazin-2-yl)methyl]-3,5-dihydro-imidazo[4,5-d]pyridazin-4-one | 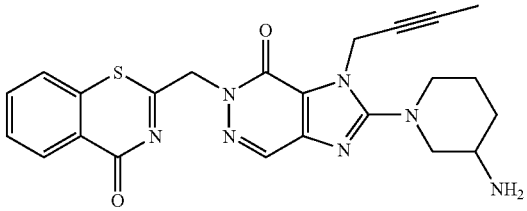 |
| (27) | 2-(3-amino-piperidin-1-yl)-3-(2-butyn-1-yl)-5-[(4H-benzo[d][1,3]thiazin-2-yl)methyl]-3,5-dihydro-imidazo[4,5-d]pyridazin-4-one | 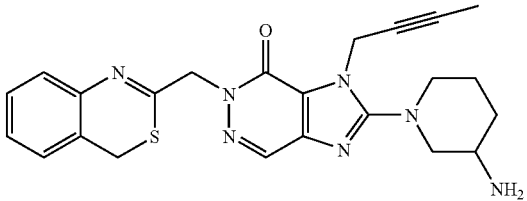 |
| (28) | 2-(3-amino-piperidin-1-yl)-3-(2-butyn-1-yl)-5-[(2H-benzo[1,4]thiazin-3-yl)methyl]-3,5-dihydro-imidazo[4,5-d]pyridazin-4-one | 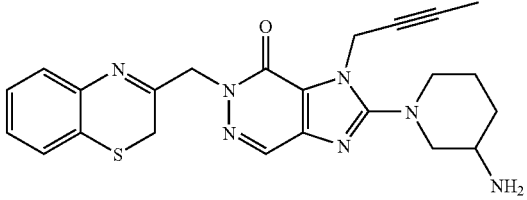 |
| (29) | 2-(3-amino-piperidin-1-yl)-3-(2-butyn-1-yl)-5-[(2-oxo-2H-benzo[e][1,3]oxazin-4-yl)methyl]-3,5-dihydro-imidazo[4,5-d]pyridazin-4-one | 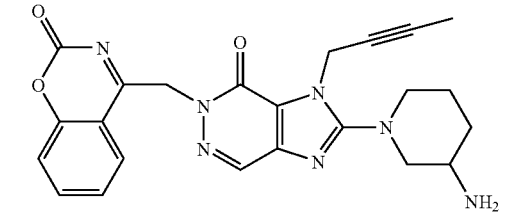 |
| (30) | 2-(3-amino-piperidin-1-yl)-3-(2-butyn-1-yl)-5-[(1-methyl-2,2-dioxo-1H-benzo[c][1,2]thiazin-4-yl)methyl]-3,5-dihydro-imidazo[4,5-d]pyridazin-4-one | 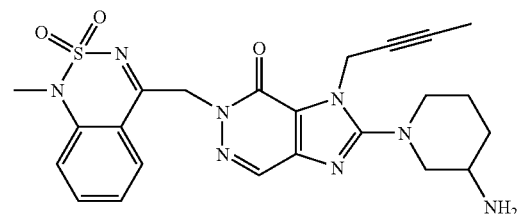 |
| (31) | 2-(3-amino-piperidin-1-yl)-3-(2-butyn-1-yl)-5-[(2,3-dihydro-1H-benzo[e][1,4]diazepin-5-yl)methyl]-3,5-dihydro-imidazo[4,5-d]pyridazin-4-one | 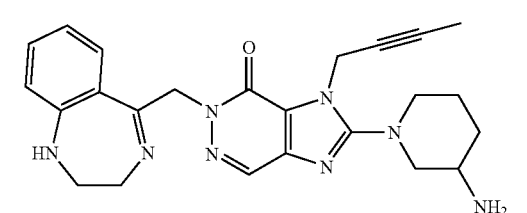 |
| (32) | 2-(3-amino-piperidin-1-yl)-3-(2-butyn-1-yl)-5-[(2-oxo-2,3-dihydro-1H-benzo[e][1,4]diazepin-5-yl)methyl]-3,5-dihydro-imidazo[4,5-d]pyridazin-4-one | 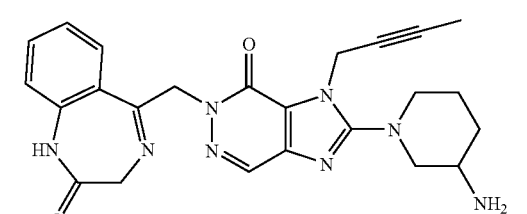 |

| No. | Name | Structural formula |
|---|---|---|
| (33) | 2-(3-amino-piperidin-1-yl)-3-(2-butyn-1-yl)-5-[(1-methyl-2,3-dihydro-1H-benzo[e][1,4]diazepin-5-yl)methyl]-3,5-dihydro-imidazo[4,5-d]pyridazin-4-one | |
| (34) | 2-(3-amino-piperidin-1-yl)-3-(2-butyn-1-yl)-5-[(1-methyl-2-oxo-2,3-dihydro-1H-benzo[e][1,4]diazepin-5-yl)methyl]-3,5-dihydro-imidazo[4,5-d]pyridazin-4-one | |
| (35) | 2-(3-amino-piperidin-1-yl)-3-(2-butyn-1-yl)-5-[(4-oxo-4,5-dihydro-3H-benzo[b][1,4]diazepin-2-yl)methyl]-3,5-dihydro-imidazo[4,5-d]pyridazin-4-one | |
| (36) | 2-(3-amino-piperidin-1-yl)-3-(2-butyn-1-yl)-5-[(5-methyl-4-oxo-4,5-dihydro-3H-benzo[b][1,4]diazepin-2-yl)methyl]-3,5-dihydro-imidazo[4,5-d]pyridazin-4-one | |
| (37) | 2-(3-amino-piperidin-1-yl)-3-(2-butyn-1-yl)-5-[5-oxo-4,5-dihydro-3H-benzo[e][1,4]diazepin-2-yl)methyl]-3,5-dihydro-imidazo[4,5-d]pyridazin-4-one | |
| (38) | 2-(3-amino-piperidin-1-yl)-3-(2-butyn-1-yl)-5-[4-methyl-5-oxo-4,5-dihydro-3H-benzo[3][1,4]diazepin-2-yl)methyl]-3,5-dihydro-imidazo[4,5-d]pyridazin-4-one | |
| (39) | 2-(3-amino-piperidin-1-yl)-3-(2-butyn-1-yl)-5-[(2,3-dihydro-benzo[f][1,4]oxazepin-5-yl)methyl]-3,5-dihydro-imidazo[4,5-d]pyridazin-4-one | |

| No. | Name | Structural formula |
|---|---|---|
| (40) | 2-(3-amino-piperidin-1-yl)-3-(2-butyn-1-yl)-5-[(3,3-dimethyl-2,3-dihydro-benzo[f][1,4]oxazepin-5-yl)methyl]-3,5-dihydro-imidazo[4,5-d]pyridazin-4-one | |
| (41) | 2-(3-amino-piperidin-1-yl)-3-(2-butyn-1-yl)-5-[(2,2-dimethyl-2,3-dihydro-benzo[f][1,4]oxazepin-5-yl)methyl]-7-methyl-3,5-dihydro-imidazo[4,5-d]pyridazin-4-one | |
| (42) | 2-(3-amino-piperidin-1-yl)-3-(2-butyn-1-yl)-5-[(2,3-dihydro-benzo[b][1,4]oxazepin-4-yl)methyl]-7-methyl-3,5-dihydro-imidazo[4,5-d]pyridazin-4-one | |
| (43) | 2-(3-amino-piperidin-1-yl)-3-(2-butyn-1-yl)-5-[(6,6-dimethyl-2,3-dihydro-benzo[b][1,4]oxazepin-4-yl)methyl]-7-methyl-3,5-dihydro-imidazo[4,5-d]pyridazin-4-one | |
| (44) | 2-(3-amino-piperidin-1-yl)-3-(2-butyn-1-yl)-5-[(2,3-dihydro-benzo[b][1,4]thiazepin-4-yl)methyl]-7-methyl-3,5-dihydro-imidazo[4,5-d]pyridazin-4-one | |
| (45) | 2-(3-amino-piperidin-1-yl)-3-(2-butyn-1-yl)-5-[(2,2-dimethyl-2,3-dihydro-benzo[b][1,4]thiazepin-4-yl)methyl]-7-methyl-3,5-dihydro-imidazo[4,5-d]pyridazin-4-one | |
| (46) | 2-(3-amino-piperidin-1-yl)-3-(2-butyn-1-yl)-5-[(2,3-dihydro-benzo[f][1,4]thiazepin-5-yl)methyl]-7-methyl-3,5-dihydro-imidazo[4,5-d]pyridazin-4-one | |

| No. | Name | Structural formula |
|---|---|---|
| (47) | 2-(3-amino-piperidin-1-yl)-3-(2-butyn-1-yl)-5-[(5-oxo-4,5-dihydro-benzo[f][1,3,4]oxadiazepin-2-yl)methyl]-7-methyl-3,5-dihydro-imidazo[4,5-d]pyridazin-4-one | |
| (48) | 2-(3-amino-piperidin-1-yl)-3-(2-butyn-1-yl)-5-[(11H-dibenzo[b,e]azepin-6-yl)methyl]-7-ethyl-3,5-dihydro-imidazo[4,5-d]pyridazin-4-one | |
| (49) | 2-(3-amino-piperidin-1-yl)-3-(2-butyn-1-yl)-5-[(11H-dibenzo[b,e]azepin-6-yl)methyl]-7-cyanomethyl-3,5-dihydro-imidazo[4,5-d]pyridazin-4-one | |
| (50) | 2-(3-amino-piperidin-1-yl)-3-(2-butyn-1-yl)-5-[(11,11-difluoro-11H-dibenzo[b,e]azepin-6-yl)methyl]-3,5-dihydro-imidazo[4,5-c]pyridin-4-one | |
| (51) | 2-(3-amino-piperidin-1-yl)-3-(2-butyn-1-yl)-5-[(11-oxo-11H-dibenzo[b,e]azepin-6-yl)methyl]-7-(2-cyanoethyl)-3,5-dihydro-imidazo[4,5-d]pyridazin-4-one | |
| (52) | 2-(3-amino-piperidin-1-yl)-3-(1-buten-1-yl)-5-[(11H-benzo[e]pyrido[3,2-b]azepin-6-yl)methyl]-7-methyl-3,5-dihydro-imidazo[4,5-d]pyridazin-4-one | |

| No. | Name |
|---|---|
| (53) | 2-(3-amino-piperidin-1-yl-(2-butyn-1-yl)-5-[(5H-1,9,10-triaza-dibenzo[a,d]cyclohepten-11-yl)methyl]-3,5-dihydro-imidazo[4,5-d]pyridin-4-one |
| (54) | 2-(3-amino-piperidin-1-yl)-3-(2-buten-1-yl)-5-[(5-methyl-5H-dibenzo[b,e][1,4]diazepin-11-yl)methyl]-7-methyl-3,5-dihydro-imidazo[4,5-d]pyridazin-4-one |
| (55) | 2-(3-amino-piperidin-1-yl)-3-(1-buten-1-yl)-5-[(dibenzo[b,f][1,4]oxazepin-11-yl)methyl]-3,5-dihydro-imidazo[4,5-c]pyridin-4-one |
| (56) | 2-(3-amino-piperidin-1-yl)-3-(2-butyn-1-yl)-5-[(dibenzo[b,f][1,4]thiazepin-11-yl)methyl]-7-methyl-3,5-dihydro-imidazo[4,5-d]pyridazin-4-one |
| (57) | 2-(3-amino-piperidin-1-yl)-3-(1-buten-1-yl)-5-[(dibenzo[b,f][1,4]thiazepin-11-yl)methyl]-3,5-dihydro-imidazo[4,5-c]pyridin-4-one |
| (58) | 2-(3-amino-piperidin-1-yl)-3-(2-butyn-1-yl)-5-[(5-oxo-dibenzo[b,f][1,4]thiazepin-11-yl)methyl]-7-methyl-3,5-dihydro-imidazo[4,5-d]pyridazin-4-one |

-continued

| No. | Name | Structural formula |
|---|---|---|
| (59) | 2-(3-amino-piperidin-1-yl)-3-(2-butyn-1-yl)-5-[(5,5-dioxo-dibenzo[b,f][1,4]-thiazepin-11-yl)methyl]-7-methyl-3,5-dihydro-imidazo[4,5-d]pyridazin-4-one | |
| (60) | 2-(3-amino-piperidin-1-yl)-3-(2-butyn-1-yl)-5-[(5H-dibenzo[a,d]cyclohepten-10-yl)methyl]-7-methyl-3,5-dihydro-imidazo[4,5-d]pyridazin-4-one | |
| (61) | 2-(3-amino-piperidin-1-yl)-3-(2-butyn-1-yl)-5-[(5-methyl-5H-dibenzo[b,f]azepin-10-yl)methyl]-7-trifluoromethyl-3,5-dihydro-imidazo[4,5-d]pyridazin-4-one | |
| (62) | 2-(3-amino-piperidin-1-yl)-3-(3-methyl-2-buten-1-yl)-5-[(phenanthridin-6-yl)methyl]-7-methyl-3,5-dihydro-imidazo[4,5-d]pyridazin-4-one | |
| (63) | 2-(3-amino-piperidin-1-yl)-3-(2-buten-1-yl)-5-[(phenanthridin-6-yl)methyl]-7-methyl-3,5-dihydro-imidazo[4,5-d]pyridazin-4-one | |

| No. | Name | Structural formula |
|---|---|---|
| (64) | 2-(3-amino-piperidin-1-yl)-3-(1-buten-1-yl)-5-[(phenanthridin-6-yl)methyl]-7-methyl-3,5-dihydro-imidazo[4,5-d]pyridazin-4-one | |
| (65) | 2-(3-amino-piperidin-1-yl)-3-[(1-cyclopenten-1-yl)methyl]-5-[(phenanthridin-6-yl)methyl]-7-methyl-3,5-dihydro-imidazo[4,5-d]pyridazin-4-one | |
| (66) | 2-(3-amino-piperidin-1-yl)-3-(1-buten-1-yl)-5-[(phenanthridin-6-yl)methyl]-3,5-dihydro-imidazo[4,5-c]pyridin-4-one | |
| (67) | 2-(3-amino-piperidin-1-yl)-3-(2-butyn-1-yl)-5-[(benzo[c][1,5]naphthyridin-6-yl)methyl]-7-cyclopropyl-3,5-dihydro-imidazo[4,5-d]pyridazin-4-one | |
| (68) | 2-(3-amino-piperidin-1-yl)-3-(2-butyn-1-yl)-5-[(benzo[h][1,6]naphthyridin-5-yl)methyl]-3,5-dihydro-imidazo[4,5-d]pyridazin-4-one | |

-continued

| No. | Name | Structural formula |
|---|---|---|
| (69) | 2-(3-amino-piperidin-1-yl)-3-(2-butyn-1-yl)-5-[(benzo[c][1,8]naphthyridin-6-yl)methyl]-3,5-dihydro-imidazo[4,5-d]pyridazin-4-one | |
| (70) | 2-(3-amino-piperidin-1-yl)-3-(2-butyn-1-yl)-5-[(5-benzo[f][1,7]naphthyridin-5-yl)methyl]-3,5-dihydro-imidazo[4,5-c]pyridin-4-one | |
| (71) | 2-(3-amino-piperidin-1-yl)-3-(2-butyn-1-yl)-5-[(1,5,9-triaza-phenanthren-10-yl)methyl]-3,5-dihydro-imidazo[4,5-c]pyridin-4-one | |
| (72) | 2-(3-amino-piperidin-1-yl)-3-(2-butyn-1-yl)-5-[(1,2,3,4-tetrahydrophenanthridin-6-yl)methyl]-3,5-dihydro-imidazo[4,5-c]pyridin-4-one | |
| (73) | 2-(3-amino-piperidin-1-yl)-3-(2-butyn-1-yl)-5-[(1,2,3,4,4a,10b-hexahydro-phenanthridin-6-yl)methyl]-3,5-dihydro-imidazo[4,5-c]pyridin-4-one | |
| (74) | 2-(3-amino-piperidin-1-yl)-3-(2-butyn-1-yl)-5-[(2,3-dihydro-1H-4-aza-cyclopenta[a]naphth-5-yl)methyl]-3,5-dihydro-imidazo[4,5-c]pyridin-4-one | |

| No. | Name | Structural formula |
|---|---|---|
| (75) | 2-(3-amino-piperidin-1-yl)-3-(2-butyn-1-yl)-5-[(8,9,10,11-tetrahydro-7H-6-aza-cyclohepta[a]naphth-5-yl)methyl]-3,5-dihydro-imidazo[4,5-c]pyridin-4-one | |
| (76) | 2-(3-amino-piperidin-1-yl)-3-(2-butyn-1-yl)-5-[(2,3-dihydro-1H-4-oxo-10-aza-phenanthren-9-yl)methyl]-3,5-dihydro-imidazo[4,5-c]pyridin-4-one | |
| (77) | 2-(3-amino-piperidin-1-yl)-3-(2-butyn-1-yl)-5-[(1-oxo-2,3-dihydro-1H-4-oxo-10-aza-phenanthren-9-yl)methyl]-3,5-dihydro-imidazo[4,5-c]pyridin-4-one | |
| (78) | 2-(3-amino-piperidin-1-yl)-3-(2-butyn-1-yl)-5-[(10-cyanophenanthren-9-yl)methyl]-3,5-dihydro-imidazo[4,5-c]pyridin-4-one | |
| (79) | 2-(3-amino-piperidin-1-yl)-3-(2-butyn-1-yl)-5-[(benzo[h]quinolin-6-yl)methyl]-3,5-dihydro-imidazo[4,5-c]pyridin-4-one | |
| (80) | 2-(3-amino-piperidin-1-yl)-3-(2-butyn-1-yl)-5-[(benzo[f]quinolin-6-yl)methyl]-3,5-dihydro-imidazo[4,5-d]pyridazin-4-one | |

-continued

| No. | Name | Structural formula |
|---|---|---|
| (81) | 2-(3-amino-piperidin-1-yl)-3-(2-butyn-1-yl)-5-[(benzo[f]quinoxalin-6-)methyl]-3,5-dihydro-imidazo[4,5-d]pyridazin-4-one | 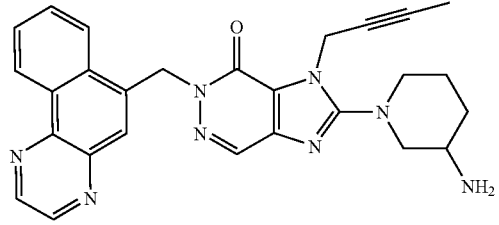 |
| (82) | 2-(3-amino-piperidin-1-yl)-3-(2-butyn-1-yl)-5-[(5H-benzo[e]pyrrolo[1,2-a][1,4]diazepin-11-yl)methyl]-7-methyl-3,5-dihydro-imidazo[4,5-d]pyridazin-4-one | 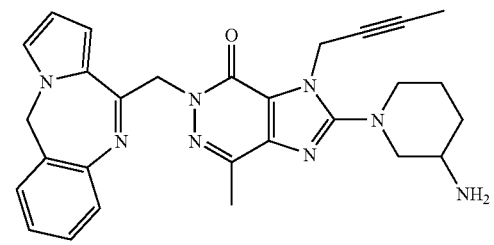 |
| (83) | 2-(3-amino-piperidin-1-yl)-3-(2-butyn-1-yl)-5-[(thieno[3,2-b][1,4]benzoxazepin-9-yl)methyl]-7-trifluoromethyl-3,5-dihydro-imidazo[4,5-d]pyridazin-4-one | 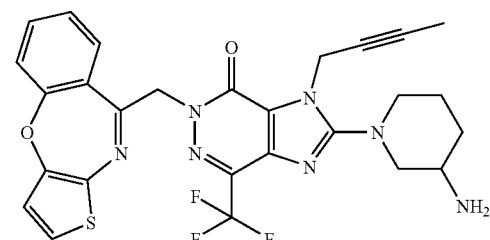 |
| (84) | 2-(3-amino-piperidin-1-yl)-3-(2-butyn-1-yl)-5-[(thieno[3,2-b][1,4]benzoxazepin-9-yl)methyl]-3,5-dihydro-imidazo[4,5-c]pyridin-4-one | 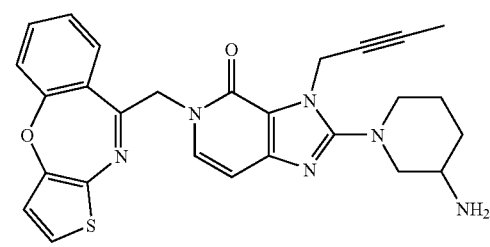 |
| (85) | 2-(3-amino-piperidin-1-yl)-3-(2-butyn-1-yl)-5-[(5H-dibenzo[d,f][1,3]diazepin-6-yl)methyl]-7-methyl-3,5-dihydro-imidazo[4,5-d]pyridazin-4-one | 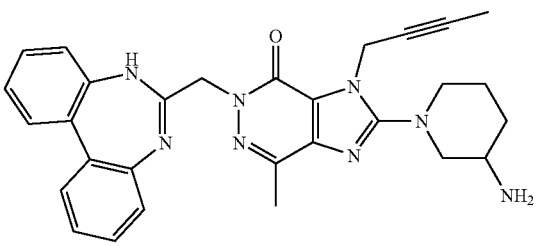 |
| (86) | 2-(3-amino-piperidin-1-yl)-3-(2-butyn-1-yl)-5-[(5-methyl-5H-dibenzo[d,f][1,3]diazepin-6-yl)methyl]-3,5-dihydro-imidazo[4,5-c]pyridin-4-one | 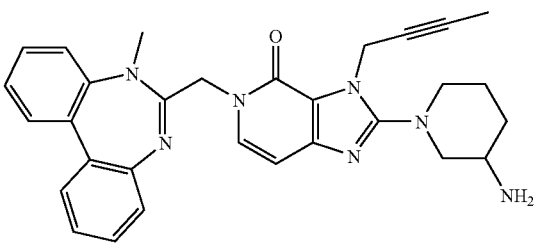 |

| No. | Name | Structural formula |
|---|---|---|
| (87) | 2-(3-amino-piperidin-1-yl)-3-(3-methylbut-2-en-1-yl)-5-[(5-oxa-7-aza-dibenzo[a,c]cyclohepten-6-yl)methyl]-7-methyl-3,5-dihydro-imidazo[4,5-c]pyridin-4-one | |
| (88) | 2-(3-amino-piperidin-1-yl)-3-(2-butyn-1-yl)-5-[(naphtho[1,2-d]thiazol-2-yl)methyl]-3,5-dihydro-imidazo[4,5-d]pyridazin-4-one | |
| (89) | 2-(3-amino-piperidin-1-yl)-3-(2-butyn-1-yl)-5-[(naphtho[2,1-d]thiazol-2-yl)methyl]-3,5-dihydro-imidazo[4,5-d]pyridazin-4-one | |
| (90) | 2-(3-amino-piperidin-1-yl)-3-(2-butyn-1-yl)-5-[(3H-naphtho[1,2-d]imidazol-2-yl)methyl]-3,5-dihydro-imidazo[4,5-d]pyridazin-4-one | |
| (91) | 2-(3-amino-piperidin-1-yl)-3-(2-butyn-1-yl)-5-[(naphtho[1,2-b]furan-2-yl)methyl]-3,5-dihydro-imidazo[4,5-d]pyridazin-4-one | |
| (92) | 2-(3-amino-piperidin-1-yl)-3-(2-butyn-1-yl)-5-[(naphtho[2,1-b]furan-2-yl)methyl]-3,5-dihydro-imidazo[4,5-d]pyridazin-4-one | |

| No. | Name | Structural formula |
|---|---|---|
| (93) | 2-(3-amino-piperidin-1-yl)-3-(2-butyn-1-yl)-5-[(2-methyl-furo[3,2-c]isoquinolin-5-yl)methyl]-3,5-dihydro-imidazo[4,5-c]pyridin-4-one | |
| (94) | 2-(3-amino-piperidin-1-yl)-3-(2-butyn-1-yl)-5-[(pyrazolo[1,5-c]quinazolin-5-yl)methyl]-3,5-dihydro-imidazo[4,5-d]pyridazin-4-one | |
| (95) | 2-(3-amino-piperidin-1-yl)-3-(2-butyn-1-yl)-5-[(1H-perimidin-2-yl)methyl]-3,5-dihydro-imidazo[4,5-d]pyridazin-4-one | |

EXAMPLE 2

Coated Tablets Containing 75 mg of Active Substance

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg
die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 3

Tablets Containing 100 mg of Active Substance

| Composition: | |
|---|---|
| 1 tablet contains: | |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 4

Tablets Containing 150 mg of Active Substance

| Composition: 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg
die: 10 mm, flat

EXAMPLE 5

Hard Gelatine Capsules Containing 150 mg of Active Substance

| 1 capsule contains: | |
|---|---|
| active substance | 150.0 mg |
| corn starch (dried) | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg
Capsule shell: size 1 hard gelatine capsule.

EXAMPLE 6

Suppositories Containing 150 mg of Active Substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 7

Suspension Containing 50 mg of Active Substance

| 100 ml of suspension contain: | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 8

Ampoules Containing 10 mg Active Substance

| Composition: | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 9

Ampoules Containing 50 mg of Active Substance

| Composition: | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:
1. A compound of formula (I)

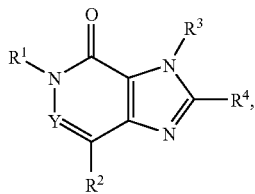

wherein
R¹ denotes a $C_{1-3}$-alkyl group substituted by a group $R_a$, where
$R_a$ denotes a 3,4-dihydro-quinolinyl, 3,4-dihydro-isoquinolinyl, 1,4-dihydro-quinazolinyl, 3,4-dihydro-quinazolinyl, 1H-benzo[d][1,2]oxazinyl, 4H-benzo[e][1,3]oxazinyl, 4H-benzo[d][1,3]oxazinyl or 2H-benzo[1,4]oxazinyl group, wherein in each case
in the benzo moiety one to three methyne groups may each be replaced by a nitrogen atom and in the heterocyclyl moiety a methylene group may be replaced by a carbonyl group,
a 4H-benzo[e][1,3]thiazinyl, 4H-benzo[d][1,3]thiazinyl or 2H-benzo[1,4]thiazinyl group wherein in each case
in the benzo moiety one to three methyne groups may each be replaced by a nitrogen atom and in the heterocyclyl moiety a methylene group may be replaced by a carbonyl group and the sulphur atom may be replaced by a sulphinyl or sulphonyl group,
a 2-oxo-2H-benzo[e][1,3]oxazinyl or 2,2-dioxo-1H-benzo[c][1,2]thiazinyl group wherein in each case in the benzo moiety
one to three methyne groups may each be replaced by a nitrogen atom,
a 2,3-dihydro-1H-benzo[e][1,4]diazepinyl, 4,5-dihydro-3H-benzo[b][1,4]diazepinyl or 5-oxo-4,5-dihydro-3H-benzo[e][1,4]diazepinyl group wherein in each case
in the benzo moiety one to three methyne groups may each be replaced by a nitrogen atom and in the heterocyclyl moiety a methylene group may be replaced by a carbonyl group,
a 2,3-dihydro-benzo[f][1,4]oxazepinyl or 2,3-dihydro-benzo[b][1,4]oxazepinyl group wherein in each case
in the benzo moiety one to three methyne groups may each be replaced by a nitrogen atom and in the heterocyclyl moiety a methylene group may be replaced by a carbonyl group,
a 2,3-dihydro-benzo[b][1,4]thiazepinyl or 2,3-dihydro-benzo[f][1,4]thiazepinyl group wherein in each case
in the benzo moiety one to three methyne groups may each be replaced by a nitrogen atom and in the heterocyclyl moiety a methylene group may be replaced by a carbonyl group and the sulphur atom may be replaced by a sulphinyl or sulphonyl group,
a 5-oxo-4,5-dihydro-benzo[f][1,3,4]oxadiazepinyl group wherein
in the benzo moiety one to three methyne groups may each be replaced by a nitrogen atom,
a 11H-dibenzo[b,e]azepinyl or 5H-dibenzo[a,d]cycloheptenyl group wherein in each case
in the benzo moiety one to three methyne groups may each be replaced by a nitrogen atom and the methylene group in the heterocyclyl moiety may be replaced by an oxygen or sulphur atom, a carbonyl, sulphinyl or sulphonyl group or by an imino group substituted by $R_x$, where
$R_x$ denotes a hydrogen atom or a $C_{1-4}$-alkyl, $C_{2-4}$-alkenyl, $C_{2-4}$-alkynyl, $C_{3-6}$-cycloalkyl, $C_{3-6}$-cycloalkyl-$C_{1-3}$-alkyl, aryl, aryl-$C_{1-3}$-alkyl, hydroxy-$C_{2-4}$-alkyl, $C_{1-3}$-alkyloxy-$C_{2-4}$-alkyl, $C_{3-6}$-cycloalkyloxy-$C_{2-4}$-alkyl, amino-$C_{2-4}$-alkyl, $C_{1-3}$-alkylamino-$C_{2-4}$-alkyl, di-($C_{1-3}$-alkyl)-amino-$C_{2-4}$-alkyl, $C_{1-3}$-alkyl-carbonyl, $C_{1-3}$-alkyloxy-carbonyl, $C_{1-3}$-alkyloxy-carbonyl-$C_{1-3}$-alkyl, aryl-carbonyl, $C_{1-3}$-alkyl-sulphonyl or aryl-sulphonyl group,
a phenanthridinyl group wherein
in the benzo moiety one to three methyne groups may each be replaced by a nitrogen atom, and
a 1,2,3,4-tetrahydro-phenanthridinyl, 1,2,3,4,4a,10b-hexahydro-phenanthridinyl, 2,3-dihydro-1H-4-aza-cyclopenta[a]naphthyl or a 8,9,10,11-tetrahydro-7H-6-aza-cyclohepta[a]naphthyl group wherein in each case
in the benzo moiety one to three methyne groups may each be replaced by a nitrogen atom and one or two methylene groups may each be replaced by an oxygen atom or a carbonyl group, while, if two methylene groups are each replaced by an oxygen atom, the oxygen atoms must be separated from one another by at least two methylene units,
a phenanthrenyl group wherein
in each case one to three of the methyne groups in position 1 to 4 and 5 to 8 may each be replaced by a nitrogen atom,
a 1,2,3,4-tetrahydro-phenanthrenyl or a 1,2,3,4,5,6,7,8-octahydro-phenanthrenyl group wherein
in each case one or two of the methylene groups in position 1 to 4 and 5 to 8 may each be replaced by an oxygen atom or a carbonyl group, while, if two methylene groups are each replaced by an oxygen atom, the oxygen atoms must be separated from one another by at least two methylene units,
a 5H-benzo[e]pyrrolo[1,2-a][1,4]diazepinyl, thieno[3,2-b][1,4]benzoxazepinyl, 5H-dibenzo[d,f][1,3]diazepinyl or a 5-oxa-7-aza-dibenzo[a,c]cycloheptenyl group wherein in each case
in the benzo moiety one to three methyne groups may each be replaced by a nitrogen atom,
a naphtho[1,2-d]oxazolyl, naphtho[2,1-d]oxazolyl, naphtho[1,2-d]thiazolyl, naphtho[2,1-d]thiazolyl, naphtho[1,2-d]imidazolyl, naphtho[1,2-b]furanyl or naphtho[2,1-b]furanyl group wherein in each case
in the naphthyl moiety one to three methyne groups may each be replaced by a nitrogen atom,
or a furo[3,2-c]isoquinolinyl, pyrazolo[1,5-c]quinazolinyl or 1H-perimidinyl group,
while the methylene and methyne groups of the above mentioned radicals $R_a$ may be substituted by the groups $R^{10}$ to $R^{13}$ and additionally by a $C_{1-3}$-alkyl group and the imino groups of the above mentioned radicals $R_a$ may be substituted by the groups $R_x$ as hereinbefore defined and
$R^{10}$ denotes a hydrogen atom,
a fluorine, chlorine, bromine or iodine atom,
a $C_{1-4}$-alkyl, hydroxy, or $C_{1-4}$-alkyloxy group,
a nitro, amino, $C_{1-3}$-alkylamino, di-($C_{1-3}$-alkyl)amino, cyano-$C_{1-3}$-alkylamino, N-(cyano-$C_{1-3}$-alkyl)-N—($C_{1-3}$-alkyl)-amino, $C_{1-3}$-alkyloxy-carbonyl-$C_{1-3}$- alkylamino, pyrrolidin-1-yl, piperidin-1-yl, morpholin-4-yl, piperazin-1-yl, or 4-($C_{1-3}$-alkyl)-piperazin-1-yl group, a $C_{1-3}$-alkyl-carbonylamino, arylcarbonylamino, aryl-$C_{1-3}$-alkyl-carbonylamino, $C_{1-3}$-alkyloxy-carbonylamino, aminocarbonylamino, $C_{1-3}$-alkylaminocarbonylamino, di-($C_{1-3}$-alkyl)aminocarbonylamino, pyrrolidin-1-yl-carbonylamino, piperidin-1-yl-carbonylamino, morpholin-4-yl-carbonylamino, piperazin-1-yl-carbonylamino or 4-($C_{1-3}$-alkyl)-piperazin-1-yl-carbonylamino, $C_{1-3}$-alkyl-sulphonylamino, bis-($C_{1-3}$-alkylsulphonyl)-amino, aminosulphonylamino, $C_{1-3}$-alkylamino-sulphonylamino, di-($C_{1-3}$-alkyl)amino-sulphonylamino, pyrrolidin-1-yl-sulphonylamino, piperidin-1-yl-sulphonylamino, morpholin-4-yl-sulphonylamino, piperazin-1-yl-sulphonylamino or 4-($C_{1-3}$-alkyl)-piperazin-1-yl-sulphonylamino, ($C_{1-3}$-alkylamino)thiocarbonylamino, ($C_{1-3}$-alkyloxy-carbonyl-amino)carbonylamino, arylsulphonylamino or aryl-$C_{1-3}$-alkyl-sulphonylamino group, an N—($C_{1-3}$-alkyl)-$C_{1-3}$-alkyl-carbonylamino, N—($C_{1-3}$-alkyl)-arylcarbonyl-amino, N—($C_{1-3}$-alkyl)-aryl-$C_{1-3}$-alkyl-carbonylamino, N—($C_{1-3}$-alkyl)-$C_{1-3}$-alkyloxy-carbonylamino, N-(aminocarbonyl)-$C_{1-3}$-alkylamino, N—($C_{1-3}$-alkyl-aminocarbonyl)-$C_{1-3}$-alkylamino, N-[di-($C_{1-3}$-alkyl)aminocarbonyl]-$C_{1-3}$-alkylamino, N—($C_{1-3}$-alkyl)-$C_{1-3}$-alkyl-sulphonylamino, N—($C_{1-3}$-alkyl)-arylsulphonylamino, or N—($C_{1-3}$-alkyl)-aryl-$C_{1-3}$-alkyl-sulphonylamino group, a 2-oxo-imidazolidin-1-yl, 2,4-dioxo-imidazolidin-1-yl, 2,5-dioxo-imidazolidin-1-yl or 2-oxo-hexahydro-pyrimidin-1-yl group wherein the nitrogen atom in the 3 position may be substituted in each case by a methyl or ethyl group, a cyano, carboxy, $C_{1-3}$-alkyloxy-carbonyl, aminocarbonyl, $C_{1-3}$-alkyl-aminocarbonyl, di-($C_{1-3}$-alkyl)-aminocarbonyl, pyrrolidin-1-yl-carbonyl, piperidin-1-yl-carbonyl, morpholin-4-yl-carbonyl, piperazin-1-yl-carbonyl or 4-($C_{1-3}$-alkyl)-piperazin-1-yl-carbonyl group, a $C_{1-3}$-alkyl-carbonyl or an arylcarbonyl group, a carboxy-$C_{1-3}$-alkyl, $C_{1-3}$-alkyloxy-carbonyl-$C_{1-3}$-alkyl, cyano-$C_{1-3}$-alkyl, aminocarbonyl-$C_{1-3}$-alkyl, $C_{1-3}$-alkyl-aminocarbonyl-$C_{1-3}$-alkyl, di-($C_{1-3}$-alkyl)-aminocarbonyl-$C_{1-3}$-alkyl, pyrrolidin-1-yl-carbonyl-$C_{1-3}$-alkyl, piperidin-1-yl-carbonyl-$C_{1-3}$-alkyl, morpholin-4-yl-carbonyl-$C_{1-3}$-alkyl, piperazin-1-yl-carbonyl-$C_{1-3}$-alkyl or 4-($C_{1-3}$-alkyl)-piperazin-1-yl-carbonyl-$C_{1-3}$-alkyl group, a carboxy-$C_{1-3}$-alkyloxy, $C_{1-3}$-alkyloxy-carbonyl-$C_{1-3}$-alkyloxy, cyano-$C_{1-3}$-alkyloxy, aminocarbonyl-$C_{1-3}$-alkyloxy, $C_{1-3}$-alkyl-aminocarbonyl-$C_{1-3}$-alkyloxy, di-($C_{1-3}$-alkyl)-aminocarbonyl-$C_{1-3}$-alkyloxy, pyrrolidin-1-yl-carbonyl-$C_{1-3}$-alkyloxy, piperidin-1-yl-carbonyl-$C_{1-3}$-alkyloxy, morpholin-4-yl-carbonyl-$C_{1-3}$-alkyloxy, piperazin-1-yl-carbonyl-$C_{1-3}$-alkyloxy or 4-($C_{1-3}$-alkyl)-piperazin-1-yl-carbonyl-$C_{1-3}$-alkyloxy group, a hydroxy-$C_{1-3}$-alkyl, $C_{1-3}$-alkyloxy-$C_{1-3}$-alkyl, amino-$C_{1-3}$-alkyl, $C_{1-3}$-alkylamino-$C_{1-3}$-alkyl, di-($C_{1-3}$-alkyl)-amino-$C_{1-3}$-alkyl, pyrrolidin-1-yl-$C_{1-3}$-alkyl, piperidin-1-yl-$C_{1-3}$-alkyl, morpholin-4-yl-$C_{1-3}$-alkyl, piperazin-1-yl-$C_{1-3}$-alkyl or 4-($C_{1-3}$-alkyl)-piperazin-1-yl-$C_{1-3}$-alkyl group, a hydroxy-$C_{1-3}$-alkyloxy, $C_{1-3}$-alkyloxy-$C_{1-3}$-alkyloxy, $C_{1-3}$-alkylsulphanyl-$C_{1-3}$-alkyloxy, $C_{1-3}$-alkylsulphinyl-$C_{1-3}$-alkyloxy, $C_{1-3}$-alkylsulphonyl-$C_{1-3}$-alkyloxy, amino-$C_{1-3}$-alkyloxy, $C_{1-3}$-alkylamino-$C_{1-3}$-alkyloxy, di-($C_{1-3}$-alkyl)-amino-$C_{1-3}$-alkyloxy, pyrrolidin-1-yl-$C_{1-3}$-alkyloxy, piperidin-1-yl-$C_{1-3}$-alkyloxy, morpholin-4-yl-$C_{1-3}$-alkyloxy, piperazin-1-yl-$C_{1-3}$-alkyloxy or 4-($C_{1-3}$-alkyl)-piperazin-1-yl-$C_{1-3}$-alkyloxy group, a mercapto, $C_{1-3}$-alkylsulphanyl, $C_{1-3}$-alkysulphinyl, $C_{1-3}$-alkylsulphonyl, $C_{1-3}$-alkylsulphonyloxy, arylsulphonyloxy, trifluoromethylsulphanyl, trifluoromethylsulphinyl or trifluoromethylsulphonyl group, a sulpho, aminosulphonyl, $C_{1-3}$-alkyl-aminosulphonyl, di-($C_{1-3}$-alkyl)-aminosulphonyl, pyrrolidin-1-yl-sulphonyl, piperidin-1-yl-sulphonyl, morpholin-4-yl-sulphonyl, piperazin-1-yl-sulphonyl or 4-($C_{1-3}$-alkyl)-piperazin-1-yl-sulphonyl group, a methyl or methoxy group substituted by 1 to 3 fluorine atoms, an ethyl or ethoxy group substituted by 1 to 5 fluorine atoms, a $C_{2-4}$-alkenyl or $C_{2-4}$-alkynyl group, a $C_{3-4}$-alkenyloxy or $C_{3-4}$-alkynyloxy group, a $C_{3-6}$-cycloalkyl or $C_{3-6}$-cycloalkyloxy group, a $C_{3-6}$-cycloalkyl-$C_{1-3}$-alkyl or $C_{3-6}$-cycloalkyl-$C_{1-3}$-alkyloxy group or an aryl, aryloxy, aryl-$C_{1-3}$-alkyl or aryl-$C_{1-3}$-alkyloxy group, $R^{11}$ and $R^{12}$, which may be identical or different, in each case represent a hydrogen atom, a fluorine, chlorine, bromine or iodine atom, a $C_{1-3}$-alkyl, trifluoromethyl, hydroxy, $C_{1-3}$-alkyloxy or cyano group, or $R^{11}$ together with $R^{12}$, if these are bound to adjacent carbon atoms, also denotes a methylenedioxy, difluoromethylenedioxy, ethylenedioxy or a straight-chain $C_{3-5}$-alkylene group and $R^{13}$ denotes a hydrogen atom, a fluorine, chlorine or bromine atom, a trifluoromethyl, $C_{1-3}$-alkyl or $C_{1-3}$-alkyloxy group, $R^2$ denotes a hydrogen atom, a $C_{1-6}$-alkyl group, or a $C_{3-6}$-cycloalkyl group, Y denotes a group of formula C—$R^5$, while $R^5$ is defined like $R^2$ and in each case one of the two groups $R^2$ and $R^5$ must be a hydrogen atom or a $C_{1-3}$-alkyl group, $R^3$ denotes a $C_{3-8}$-alkyl group, a $C_{3-8}$-alkenyl group, or a $C_{3-8}$-alkynyl group, and $R^4$ denotes a piperidin-1-yl group which is substituted in the 3 position by an amino, $C_{1-3}$-alkylamino or a di-($C_{1-3}$-alkyl)amino, while by the aryl groups mentioned in the definition of the above groups are meant phenyl or naphthyl groups which may be mono- or disubstituted by $R_h$, while the substituents may be identical or different and $R_h$ denotes a fluorine, chlorine, bromine or iodine atom, a trifluoromethyl, cyano, nitro, amino, aminocarbonyl, aminosulphonyl, methylsulphonyl, acetylamino, methylsulphonylamino, $C_{1-3}$-alkyl, cyclopropyl, ethenyl, ethynyl, hydroxy, $C_{1-3}$-alkyloxy, difluoromethoxy or trifluoromethoxy group, by the heteroaryl groups mentioned in the definition of the above groups are meant a pyrrolyl, furanyl, thienyl, pyridyl, indolyl, benzofuranyl, benzothiophenyl, quinolinyl or isoquinolinyl group, or a pyrrolyl, furanyl, thienyl or pyridyl group, wherein one or two methyne groups are replaced by nitrogen atoms, or an indolyl, benzofuranyl, benzothiophenyl, quinolinyl or isoquinolinyl group, wherein one to three methyne groups are replaced by nitrogen atoms, and the above mentioned heteroaryl groups may be mono- or disubstituted by $R_h$, while the substituents may be identical or different and $R_h$ is as hereinbefore defined, while, unless otherwise stated, the above mentioned alkyl, alkenyl and alkynyl groups may be straight-chain or branched, and the hydrogen atoms of the methyl or ethyl groups contained in the definitions may be wholly or partly replaced by fluorine atoms, or a tautomer, enantiomer, diastereomer, mixture thereof, or salt thereof.

2. The compound of formula I according to claim 1, wherein $R^1$ denotes a methyl group substituted by a group $R_a$, where $R_a$ denotes a 3,4-dihydro-quinolinyl group, a 3,4-dihydro-isoquinolinyl group, a 1,4-dihydro-quinazolinyl or 4-oxo-1,4-dihydro-quinazolinyl group, a 3,4-dihydro-quinazolinyl or 4-oxo-3,4-dihydro-quinazolinyl group, a 1H-benzo[d][1,2]oxazinyl or 1-oxo-1H-benzo[d][1,2]oxazinyl group, a 4H-benzo[e][1,3]oxazinyl or 4-oxo-4H-benzo[e][1,3]oxazinyl group, a 4H-benzo[d][1,3]oxazinyl or 4-oxo-4H-benzo[d][1,3]oxazinyl group, a 2H-benzo[1,4]oxazinyl or 2-oxo-2H-benzo[1,4]oxazinyl group, a 4H-benzo[e][1,3]thiazinyl or 4-oxo-4H-benzo[e][1,3]thiazinyl group, a 4H-benzo[d][1,3]thiazinyl or 2H-benzo[1,4]thiazinyl group, a 2-oxo-2H-benzo[e][1,3]oxazinyl or 2,2-dioxo-1H-benzo[c][1,2]thiazinyl group, a 2,3-dihydro-1H-benzo[e][1,4]diazepinyl or 2-oxo-2,3-dihydro-1H-benzo[e][1,4]diazepinyl group, a 4,5-dihydro-3H-benzo[b][1,4]diazepinyl or 4-oxo-4,5-dihydro-3H-benzo[b][1,4]diazepinyl group, a 5-oxo-4,5-dihydro-3H-benzo[e][1,4]diazepinyl group, a 2,3-dihydro-benzo[f][1,4]oxazepinyl or 2,3-dihydro-benzo[b][1,4]oxazepinyl group, a 2,3-dihydro-benzo[f][1,4]thiazepinyl or 2,3-dihydro-benzo[b][1,4]thiazepinyl group, a 5-oxo-4,5-dihydro-benzo[f][1,3,4]oxadiazepinyl group, a 11H-dibenzo[b,e]azepinyl or 11-oxo-11H-dibenzo[b,e]azepinyl group, a 11H-benzo[e]pyrido[3,2-b]azepinyl or a 5H-1,9,10-triaza-dibenzo[a,d]-cycloheptenyl group, a 5H-dibenzo[b,e][1,4]diazepinyl or dibenzo[b,f][1,4]oxazepinyl group, a dibenzo[b,f][1,4]thiazepinyl, 5-oxo-dibenzo[b,f][1,4]thiazepinyl or 5,5-dioxo-dibenzo[b,f][1,4]thiazepinyl group, a 5H-dibenzo[a,d]cycloheptenyl or 5H-dibenzo[b,f]azepinyl group, a phenanthridinyl, benzo[c][1,5]naphthyridinyl, benzo[h][1,6]naphthyridinyl, benzo[c][1,8]naphthyridinyl, benzo[f][1,7]naphthyridinyl or 1,5,9-triaza-phenanthrenyl group, a 1,2,3,4-tetrahydro-phenanthridinyl, 1,2,3,4,4a,10b-hexahydro-phenanthridinyl, 2,3-dihydro-1H-4-aza-cyclopenta[a]naphthyl or 8,9,10,11-tetrahydro-7H-6-aza-cyclohepta[a]naphthyl group, a 2,3-dihydro-1H-4-oxa-10-aza-phenanthrenyl or 1-oxo-2,3-dihydro-1H-4-oxa-10-aza-phenanthrenyl group, a phenanthrenyl, benzo[h]quinolinyl, benzo[f]quinolinyl or benzo[f]quinoxalinyl group, a 5H-benzo[e]pyrrolo[1,2-a][1,4]diazepinyl, thieno[3,2-b][1,4]benzoxazepinyl, 5H-dibenzo[d,f][1,3]diazepinyl or 5-oxa-7-aza-dibenzo[a,c]cycloheptenyl group, a naphtho[1,2-d]oxazolyl, naphtho[2,1-c]oxazolyl, naphtho[1,2-d]thiazolyl, naphtho[2,1-c]thiazolyl, naphtho[1,2-d]imidazolyl, naphtho[1,2-b]furanyl or naphtho[2,1-b]furanyl group, or a furo[3,2-c]isoquinolinyl, pyrazolo[1,5-c]quinazolinyl or 1H-perimidinyl group, while the benzo groups of the above mentioned radicals $R_a$ are substituted by the groups $R^{10}$ to $R^{13}$ and the alkylene units of the above mentioned groups $R_a$ may be substituted by one or two fluorine atoms or one or two $C_{1-3}$-alkyl or $C_{1-3}$-alkyloxy-carbonyl groups and the imino groups of the above mentioned radicals $R_a$ may be substituted by a $C_{1-3}$-alkyl group and $R^{10}$ denotes a hydrogen atom, a fluorine, chlorine, bromine or iodine atom, a $C_{1-3}$-alkyl or cyclopropyl group, a hydroxy, $C_{1-3}$-alkyloxy or cyclopropyloxy group, a nitro, amino, $C_{1-3}$-alkylamino or di-($C_{1-3}$-alkyl)amino group, a $C_{1-3}$-alkyl-carbonylamino or $C_{1-3}$-alkyl-sulphonylamino group, a cyano, carboxy, $C_{1-3}$-alkyloxy-carbonyl, aminocarbonyl, $C_{1-3}$-alkyl-aminocarbonyl or di-($C_{1-3}$-alkyl)-aminocarbonyl group, a mercapto, $C_{1-3}$-alkylsulphanyl, $C_{1-3}$-alkysulphinyl, $C_{1-3}$-alkylsulphonyl or aminosulphonyl group or a difluoromethyl, trifluoromethyl, difluoromethoxy or trifluoromethoxy group and $R^{11}$, $R^{12}$ and $R^{13}$, which may be identical or different, in each case represent a hydrogen atom, a fluorine, chlorine or bromine atom, a methyl, trifluoromethyl or methoxy group, $R^2$ denotes a hydrogen atom or a $C_{1-3}$-alkyl, cyclopropyl or trifluoromethyl group, Y denotes a group of formula C—$R^5$, while $R^5$ denotes a hydrogen atom or a $C_{1-3}$-alkyl group, $R^3$ denotes a 2-buten-1-yl or 3-methyl-2-buten-1-yl group, a 1-buten-1-yl group, or a 2-butyn-1-yl group and $R^4$ denotes a (3-amino-piperidin-1-yl) group, while, unless otherwise stated, the above mentioned alkyl groups may be straight-chain or branched, or a tautomer, enantiomer, diastereomer, mixture thereof, or salt thereof.

3. The compound of formula I according to claim 2, wherein

R¹ denotes a methyl group substituted by a group R$_a$, where R$_a$ denotes a 3,4-dihydro-quinolin-2-yl group,
- a 3,4-dihydro-isoquinolin-1-yl group,
- a 1,4-dihydro-quinazolin-2-yl or 4-oxo-1,4-dihydro-quinazolin-2-yl group,
- a 3,4-dihydro-quinazolin-2-yl or 4-oxo-3,4-dihydro-quinazolin-2-yl group,
- a 1H-benzo[d][1,2]oxazin-4-yl or 1-oxo-1H-benzo[d][1,2]oxazin-4-yl group,
- a 4H-benzo[e][1,3]oxazin-2-yl or 4-oxo-4H-benzo[e][1,3]oxazin-2-yl group,
- a 4H-benzo[d][1,3]oxazin-2-yl or 4-oxo-4H-benzo[d][1,3]oxazin-2-yl group,
- a 2H-benzo[1,4]oxazin-3-yl or 2-oxo-2H-benzo[1,4]oxazin-3-yl group,
- a 4H-benzo[e][1,3]thiazin-2-yl or 4-oxo-4H-benzo[e][1,3]thiazin-2-yl group,
- a 4H-benzo[d][1,3]thiazin-2-yl or 2H-benzo[1,4]thiazin-3-yl group,
- a 2-oxo-2H-benzo[e][1,3]oxazin-4-yl or 2,2-dioxo-1H-benzo[c][1,2]thiazin-4-yl group,
- a 2,3-dihydro-1H-benzo[e][1,4]diazepin-5-yl or 2-oxo-2,3-dihydro-1H-benzo[e][1,4]diazepin-5-yl group,
- a 4,5-dihydro-3H-benzo[b][1,4]diazepin-2-yl or 4-oxo-4,5-dihydro-3H-benzo[b][1,4]diazepin-2-yl group,
- a 5-oxo-4,5-dihydro-3H-benzo[e][1,4]diazepin-2-yl group,
- a 2,3-dihydro-benzo[f][1,4]oxazepin-5-yl or 2,3-dihydro-benzo[b][1,4]oxazepin-4-yl group,
- a 2,3-dihydro-benzo[f][1,4]thiazepin-5-yl or 2,3-dihydro-benzo[b][1,4]thiazepin-4-yl group,
- a 5-oxo-4,5-dihydro-benzo[f][1,3,4]oxadiazepin-2-yl group,
- a 11H-dibenzo[b,e]azepin-6-yl or 11-oxo-11H-dibenzo[b,e]azepin-6-yl group,
- a 11H-benzo[e]pyrido[3,2-b]azepin-6-yl or a 5H-1,9,10-triaza-dibenzo[a,d]-cyclohepten-11-yl group,
- a 5H-dibenzo[b,e][1,4]diazepin-11-yl or dibenzo[b,f][1,4]oxazepin-11-yl group,
- a dibenzo[b,f][1,4]thiazepin-11-yl, 5-oxo-dibenzo[b,f][1,4]thiazepin-11-yl or 5,5-dioxo-dibenzo[b,f][1,4]thiazepin-11-yl group,
- a 5H-dibenzo[a,d]cyclohepten-10-yl or 5H-dibenzo[b,f]azepin-10-yl group,
- a phenanthridin-6-yl, benzo[c][1,5]naphthyridin-6-yl, benzo[h][1,6]naphthyridin-5-yl, benzo[c][1,8]naphthyridin-6-yl, benzo[f][1,7]naphthyridin-5-yl or 1,5,9-triaza-phenanthren-10-yl group,
- a 1,2,3,4-tetrahydro-phenanthridin-6-yl, 1,2,3,4,4a,10b-hexahydro-phenanthridin-6-yl, 2,3-dihydro-1H-4-aza-cyclopenta[a]naphth-5-yl or 8,9,10,11-tetrahydro-7H-6-aza-cyclohepta[a]naphth-5-yl group,
- a 2,3-dihydro-1H-4-oxa-10-aza-phenanthren-9-yl or 1-oxo-2,3-dihydro-1H-4-oxa-10-aza-phenanthren-9-yl group,
- a phenanthren-9-yl, benzo[h]quinolin-6-yl, benzo[f]quinolin-6-yl or benzo[f]quinoxalin-6-yl group,
- a 5H-benzo[e]pyrrolo[1,2-a][1,4]diazepin-11-yl, thieno[3,2-b][1,4]benzoxazepin-9-yl, 5H-dibenzo[d,f][1,3]diazepin-6-yl or 5-oxa-7-aza-dibenzo[a,c]cyclohepten-6-yl group,
- a naphtho[1,2-d]oxazol-2-yl, naphtho[2,1-d]oxazol-2-yl, naphtho[1,2-d]thiazol-2-yl, naphtho[2,1-d]thiazol-2-yl, naphtho[1,2-d]imidazol-2-yl, naphtho[1,2-b]furan-2-yl or naphtho[2,1-b]furan-2-yl group,
- or a furo[3,2-c]isoquinolin-5-yl, pyrazolo[1,5-c]quinazolin-5-yl or 1H-perimidin-2-yl group, while the benzo groups of the above mentioned radicals R$_a$ are substituted by the groups R¹⁰ to R¹³ and the alkylene units of the above mentioned groups R$_a$ may be substituted by one or two fluorine atoms or one or two methyl groups and the imino groups of the above mentioned radicals R$_a$ may be substituted by a methyl group and R¹⁰ denotes a hydrogen atom,
- a fluorine, chlorine, bromine or iodine atom,
- a methyl or ethyl group,
- a hydroxy, methoxy or ethoxy group or
- a difluoromethyl, trifluoromethyl, difluoromethoxy, or trifluoromethoxy group and R¹¹, R¹² and R¹³, which may be identical or different, each denote a hydrogen, fluorine, chlorine or bromine atom or a methyl, trifluoromethyl or methoxy group, R² denotes a hydrogen atom or
a methyl, trifluoromethyl, ethyl, propyl, cyclopropyl or isopropyl group, Y denotes a group of formula C—R⁵,
while R⁵ denotes a hydrogen atom or a methyl, ethyl, propyl or isopropyl group, R³ denotes a 2-buten-1-yl or 3-methyl-2-buten-1-yl group,
a 1-buten-1-yl group, or
a 2-butyn-1-yl group
and R⁴ denotes a (3-amino-piperidin-1-yl) group, or a tautomer, enantiomer, diastereomer, mixture thereof, or salt thereof.

4. A physiologically acceptable salt of the compound according to claim 1 with an inorganic or organic acid.

5. A pharmaceutical composition containing a compound according to claim 1 or a salt with an inorganic or organic acid optionally together with one or more inert carriers and/or diluents.

* * * * *